US008622747B2

(12) United States Patent
Chu et al.

(10) Patent No.: US 8,622,747 B2
(45) Date of Patent: *Jan. 7, 2014

(54) TRAINING SYSTEM AND METHOD USING A DYNAMIC PERTURBATION PLATFORM

(75) Inventors: Jeffrey J. Chu, Norwich, VT (US); Richard M. Greenwald, Norwich, VT (US); David D. Johnson, Lebanon, NH (US)

(73) Assignee: Simbex LLC, Lebanon, NH (US)

( * ) Notice: Subject to any disclaimer, the term of this patent is extended or adjusted under 35 U.S.C. 154(b) by 331 days.

This patent is subject to a terminal disclaimer.

(21) Appl. No.: 13/182,575

(22) Filed: Jul. 14, 2011

(65) Prior Publication Data
US 2011/0312473 A1 Dec. 22, 2011

Related U.S. Application Data

(63) Continuation-in-part of application No. 11/294,942, filed on Dec. 6, 2005, now Pat. No. 7,980,856.

(60) Provisional application No. 60/675,768, filed on Apr. 28, 2005.

(51) Int. Cl.
G09B 19/00 (2006.01)

(52) U.S. Cl.
USPC .......................................................... 434/258

(58) Field of Classification Search
USPC ........... 434/258; 600/592, 595, 587; 482/8, 9, 482/900; 362/102
See application file for complete search history.

(56) References Cited

U.S. PATENT DOCUMENTS

| | | |
|---|---|---|
| 4,743,008 A | 5/1988 | Fermaglich et al. |
| 5,052,406 A | 10/1991 | Nashner |
| 5,209,240 A | 5/1993 | Jain et al. |
| 5,299,454 A | 4/1994 | Fuglewicz et al. |
| 5,337,757 A | 8/1994 | Jain et al. |
| 5,474,087 A | 12/1995 | Nashner |
| 5,575,294 A | 11/1996 | Perry et al. |
| 5,582,561 A | 12/1996 | Gonzalez |
| 5,623,944 A | 4/1997 | Nashner |
| 5,830,162 A | 11/1998 | Giovannetti |
| 5,980,429 A | 11/1999 | Nashner |

(Continued)

OTHER PUBLICATIONS

Shimada Hiroyuki, et al., "New Intervention Program for Preventing Falls Among Frail Elderly People", American Journal of Physical Medicine & Rehabilitation, vol. 83, No. 7, pp. 493-499, Lippincott Williams & Wilkins, (Jul. 2004).

(Continued)

*Primary Examiner* — Timothy A Musselman
(74) *Attorney, Agent, or Firm* — Barlow, Josephs & Holmes, Ltd.

(57) ABSTRACT

A new apparatus, system and method for fall prevention training is provided that delivers, studies and analyzes the biomechanics of a disturbance event, such as a slip or trip incident, so that an appropriate response can be executed by the person to reduce or eliminate the number of falls experienced. The apparatus includes a platform that delivers a disturbance event in less than about 500 ms and preferably in the range of about 100 ms to about 200 ms. The method includes a unique protocol for fall prevention training using the apparatus. The disturbance event can create instability in the joint of the individual. An individual's walking gait can be monitored with the portions thereof detected. A disturbance event can be triggered when a given portion of the walking gait is detected. Also, the disturbance even can be triggered manually, at preset intervals or according to preset script.

10 Claims, 18 Drawing Sheets

(56) References Cited

U.S. PATENT DOCUMENTS

| | | |
|---|---|---|
| 6,010,465 A | 1/2000 | Nashner |
| 6,063,046 A | 5/2000 | Allum |
| 6,162,151 A | 12/2000 | Tani et al. |
| 6,231,527 B1 | 5/2001 | Sol |
| 6,436,009 B1 | 8/2002 | Marucci |
| 6,558,304 B1 | 5/2003 | Bardon et al. |
| 6,645,126 B1 | 11/2003 | Martin et al. |
| 6,682,351 B1 | 1/2004 | Abraham-Fuchs et al. |
| 7,980,856 B2 | 7/2011 | Grabiner et al. |
| 2002/0115536 A1 | 8/2002 | Hojo et al. |

OTHER PUBLICATIONS

Jaffe.pdf—"Stepping Over Obstacles to Improve Walking in Individuals With Post Stroke Hemiplegia"—Journal of Rehabilitation Research and Development—May/Jun. 2004—vol. 41, No. 3A, pp. 283-292.

Chmielewski, Terese L. et al., "Perturbation Training Improves Knee Kinematics and Reduces Muscle Co-contraction After Complete Unilateral Anterior Cruciate Ligament Rupture", Research Report, Thysical Therapy—vol. 85, Nov. 8, Aug. 2005.

Hartigan, Erin et al., "Perturbation Training prior to ACL Reconstruction Improves Gait Asymmetries in Non-Copers", Journal of Orthopaedic Research, pp. 724-729, Jun. 2009.

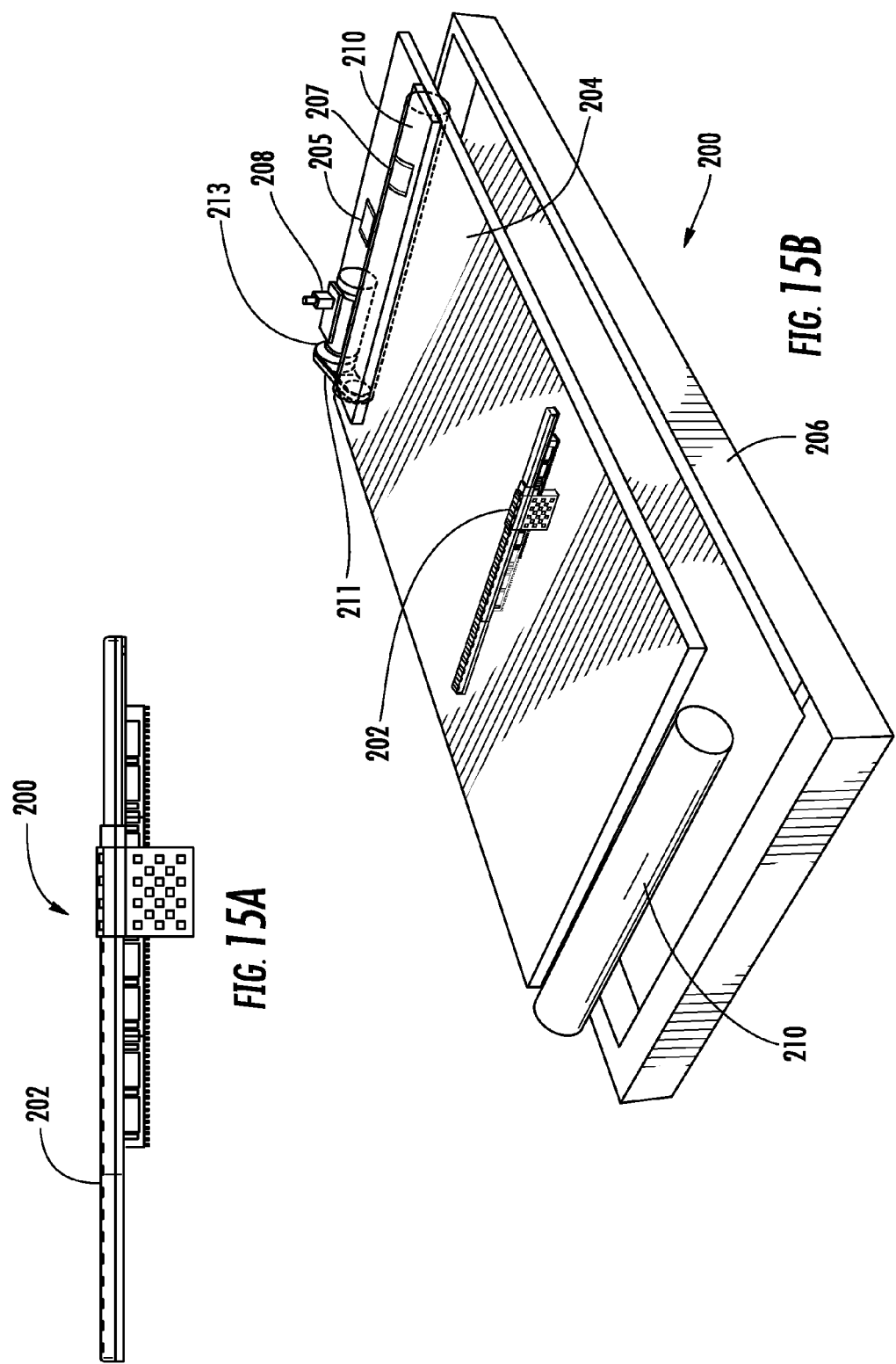

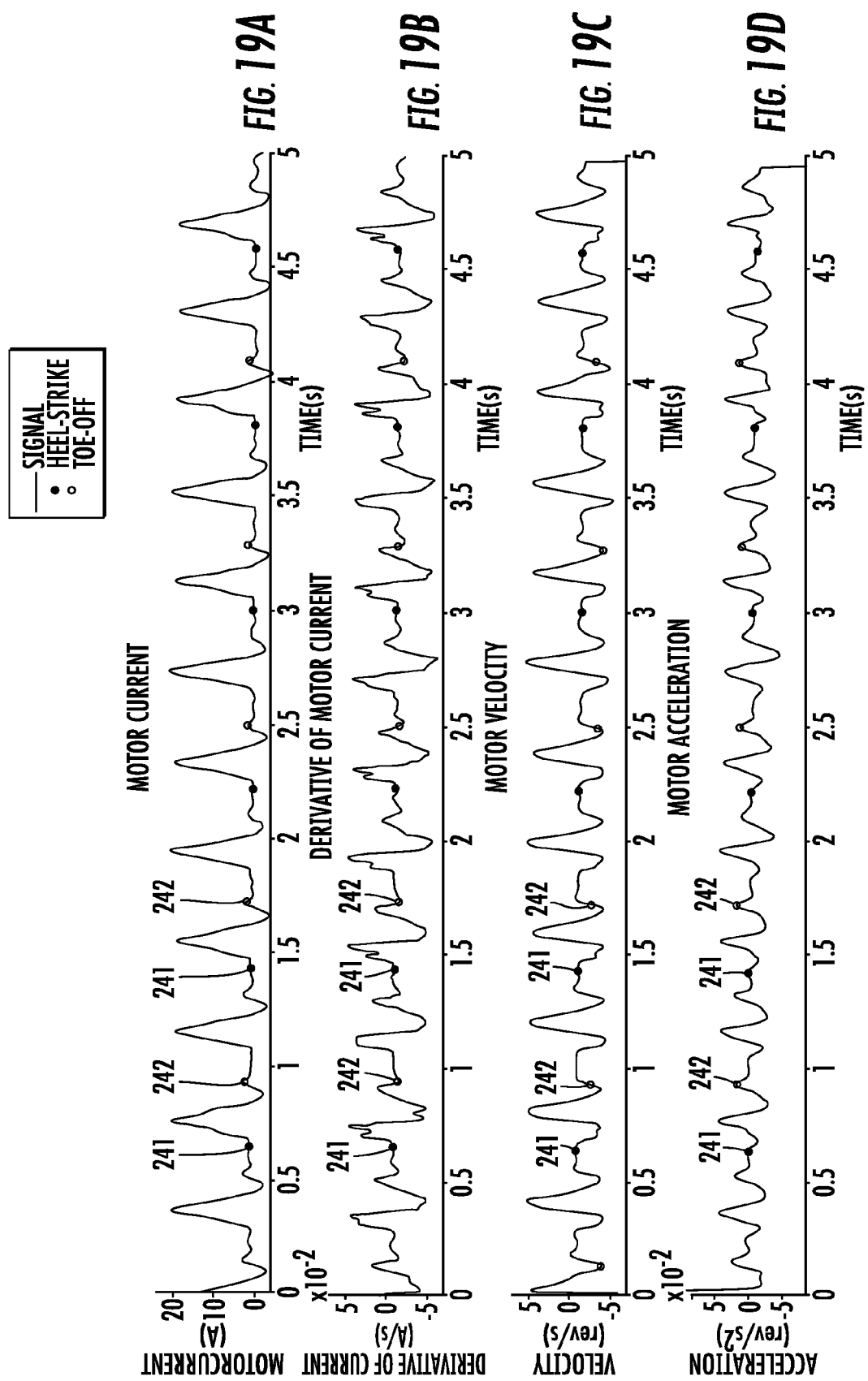

TRAINING SYSTEM AND METHOD USING A DYNAMIC PERTURBATION PLATFORM

CROSS REFERENCE TO RELATED APPLICATION

This application is a continuation-in-part of Ser. No. 11/294,942, filed Dec. 6, 2005, which is related to and claims priority from earlier filed provisional patent application Ser. No. 60/675,768, filed Apr. 28, 2005, all of which is incorporated herein by reference.

BACKGROUND OF THE INVENTION

The present invention generally relates to the human performance, sports medicine and medical rehabilitation field. More specifically, the present invention relates to a method for fall prevention training using a dynamic perturbation platform to improve the study and research of the biomechanics of trip, slip, and laterally-directed postural disturbances by a person and the step recovery thereof. Additionally, the present invention relates to human performance, injury prevention and neuromuscular training using a dynamic perturbation platform to train step responses to anterior, posterior or laterally-directed postural perturbations. Additionally, the present invention relates to neuromuscular training around any body joint response to dynamic perturbations of the body joint or multiple body joints.

It is well known in the medical field that a slip or trip during walking or standing can lead to a fall and be a serious cause of injury. This is particularly problematic for elderly people where such injuries are a leading cause of mortality. It is well known that many of these injuries can be prevented or their severity lessened if the person uses an effective strategy and technique for responding to a fall situation. Therapeutic Interventions can reduce the likelihood of a fall from a disturbance event, such as a trip or slip incident. Exercise and physical training can be used to develop strength, balance and coordination. Also, the person's environment can be changed to remove obstacles and other hazards that can cause a slip or trip. Bars and hand rails can be provided to assist walking and standing. Padded garments can be worn by the person to reduce the injury caused by the slip or fall.

An alternative approach is to study why a person falls and train them to better recover from a slip or trip to avoid a fall by taking a corrective step response. Therefore, the biomechanics of a slip or fall can be studied to better understand clinically effective ways to prevent such falls due to a slip or trip. As part of the study and analysis of disturbance events, including slip and trip incidents, it is highly desirable to be able to monitor a slip or fall incident in a controlled environment to produce data that is usable for effective training to help persons adapt their strategy for responding to a slip or trip incident.

It is also well known in the medical field that dynamic stability of a body joint is important for injury prevention. The ligaments and tendons and musculature that cross body joints prevent excessive motion of the joint that leads to injury of the structures both within and surrounding the joint. The benefits of neuromuscular training are known to provide increased endurance, positional awareness, performance and reduction in injury risk.

Specifically with respect to the knee, neuromuscular training also increases dynamic knee stiffness, dynamic knee stability, and athlete agility. Human locomotion uses sensory information and motor reflex to modulate pre-programmed motor control patterns in order to adapt to unexpected changes in the external environment. Proprioceptive information is used to maintain postural and joint stability. In human locomotion there are major kinematic events where joint stability might be needed most. These events differ for walking and running. All around the body, joint stability is attributed to joint stiffness that occurs with co-contraction of antagonistic muscles around a joint. Increased joint stiffness is believed to resist sudden joint displacements more effectively reducing the incidence of joint subluxation.

More specifically, it is well known in the medical field that ligament and other soft tissue injuries are a significant problem among people who engage in cutting, jumping, and pivoting activities, particularly young athletes and women. One ligament that is often injured, for example, is the anterior cruciate ligament (ACL) in the knee. For ACL injured athletes, neuromuscular training has improved functional outcome and increased likelihood of return to previous activity levels with decreased likelihood of knee giving way episodes. Similar effects and results can occur following soft tissue injuries to other structures and joints in the body, and are not limited to the ACL.

Following ACL or other soft tissue injury, both surgical and non-surgical treatment options exist, with the ultimate goal of regaining dynamic joint stability, and in the case of the knee joint, normal knee kinematics, and symmetrical quadriceps strength between legs. These outcomes are critical for full return of dynamic knee function and returning to pre-injury activity levels, as well as for preventing additional injury to the cartilage and the meniscus in the knee which might lead to an increased likelihood of osteoarthritis (OA).

Laboratory research has demonstrated clinically relevant effects of perturbation of support surface training for both ACL-deficient (ACL-D) and ACL-reconstructed (ACL-R) populations, particularly in females. Currently, perturbation training systems and methods are limited to balance boards that are manually pushed or pulled by physical therapists, and may not simulate real-life or sport-specific perturbations. Specifically, balance boards do not allow for perturbations that occur during an actual step. The manual perturbation method does not allow for repeatable timing of perturbations at specific phases of the gait cycle, nor can the perturbations be delivered in less than 500 ms.

ACL injuries are extremely common, with approximately 100,000-250,000 ACL reconstructions being performed annually in the United States. While males comprise a majority of all ACL injuries females are at 3-6× greater risk of suffering an ACL rupture than males. Rehabilitation is time-consuming; time from injury to completing postoperative rehabilitation can range from a few months to a year or more, and surgical intervention does not ensure a return to previous activity levels. At an estimated cost of $17,000 per ACL reconstruction and physical therapy services, expenses for this injury may exceed $1 Billion annually in the United States alone.

The ACL plays a principal role in maintaining normal knee function and stability. Quadriceps strength deficits and ACL rupture independently increase the likelihood of developing knee osteoarthritis (OA). ACL injury often leads to knee instability, quadriceps weakness, gait deviations, and post-traumatic OA. Aberrant movement and abnormal muscular strategies are common in the ACL-deficient athlete. Snyder-Mackler and colleagues developed and validated a functional screening examination as a clinical tool to identify those who have the potential to compensate well for the injury (potential-copers). Non-candidates, or non-copers, were classified by their poor functional performance and episodes of knee instability. Recurrent give way episodes of the ACL deficient knee in non-copers are likely due to their inability to stabilize their injured knee with appropriate muscle activity. Rudolph et al. defined the neuromuscular behaviors of ACL deficient athletes, and found an ineffective knee stiffening strategy characteristic of non-copers. Non-copers excessively co-contract their thigh and hamstring muscle and truncate their knee motion which may further exacerbate the alterations in joint loading and cause degenerative changes to the underlying cartilage. Persons who present with a combination of aberrant gait patterns, quadriceps weakness, and knee instability in response to an ACL rupture are at significantly increased risk of developing post-traumatic knee OA. Therefore, the importance of restoring normal gait kinematics and kinetics in this population has been underscored by many research groups.

Quadriceps weakness and knee instability can also lead to a knee stiffening strategy in an attempt to improve stability during dynamic activities, such as walking, jogging, stair climbing, and balancing on one limb. This strategy is used predominantly by athletes who are non-copers. Hartigan et al. demonstrated that perturbation training was able to restore symmetric knee excursions in this cohort, something that was not achieved by strength training alone. Again, this perturbation training was performed manually.

Clinical rehabilitation paradigms for non-operative treatment and post-operative rehabilitation following ACL rupture focus on reducing joint effusion, increasing knee range of motion, increasing quadriceps and hamstring muscle strength, functional activity education and training, agility training, and protective bracing. However, these approaches may only be successful for patients that are more sedentary or are willing to modify their physical activity levels. Common clinical techniques used during rehabilitation after ACL reconstruction are often limited to strength training, task-specific exercises, and static balance exercises. For athletes, proper coordination of muscle activity is also critical for improving dynamic knee stability and ultimately, sport performance.

After ACL injury, the quadriceps and hamstrings have diminished ability to dynamically stabilize the knee due to disruption of the mechanoreceptors in and around the knee joint. Task-specific manual perturbation training has been shown to enhance the restoration of dynamic stability in ACL deficient patients. Factors that are modulated during perturbation training include predictability, speed, direction, amplitude, and intensity of the perturbation. Snyder-Mackler and colleagues combine progressively challenging manual perturbation training together with sport-specific task training in order to achieve improvements in dynamic knee stability. Snyder-Mackler and other researchers published the results of their studies and have demonstrated the following:

Superior return to functional activity in potential copers when compared to standard rehab programs (e.g. strength training). 93% of patients using manual perturbation training returned to high-level activity without episodes of giving way. In contrast, only 50% of those who received traditional therapy returned to high-level activity.

Patients undergoing perturbation training increased their likelihood of success (i.e. no episodes of knee giving way) by 4.9× when compared to standard treatments, including strength and agility training.

Improved dynamic knee stability in ACL deficient patients through improved neuromuscular changes.

Increased Lysholm Knee Rating Scale scores compared to subjects who received standard strength training rehabilitation.

Normal quadriceps and hamstring activations and increased active stiffness. These changes may prophylactically reduce the risk of biomechanical strain injury in high-risk populations.

Manual perturbation training significantly improved lower leg dynamic muscle control in healthy young athletes. Young women responded favorably to perturbation training by mitigating their quadriceps dominance and activating their hamstrings earlier in stance, thus restoring healthier muscle activation patterns.

Manual perturbation training in conjunction with strength training improved dynamic knee stability, knee range of motion during midstance, and limb symmetry compared to strength training alone.

While manual perturbation paradigms are effective at resolving aberrant neuromuscular strategies in ACL-deficient individuals, the time required to administer the treatment may not allow the therapist time to address other patient impairments. Manual perturbation training does not address the idea of providing the perturbation during the walking cycle or while running. Additionally, manual perturbation training may not allow for timed perturbations at specific phases of the gait cycle, or at specific joint positions, velocities or joint forces. Manual perturbation do not allow for timed and controlled perturbations at specific velocities of a given joint.

Conversely, the present invention overcomes the limitations of manual perturbation methods. In the present invention, perturbations can be triggered manually, or, when desired, on a timed basis or other pre-set schedule. The timing of perturbations can be based on intrinsic physiologic factors, such as phase of the gait cycle, position, velocity or acceleration of a limb or joint. The timing of perturbations based on specific phases of gait, perturbation and automatic speed adjustments can be based on the timing and phasing of braking and propulsion of the limb being monitored.

Additionally, the timing of perturbations can be based on extrinsic factors.

There exists relationships among neuromuscular timing and external cues or triggers. Existing systems such as Nike+, a product of Nike, Inc., modify target exercise parameters based on music selected. Alternatively, it is possible to modulate the speed, pitch, volume, beat, and other rhythmic patterns of music played or presented to a user as a function of the exercise being performed or prescribed. In a similar fashion, visual stimuli such as video presentations or tactile stimuli or other external stimuli can be used in either an excitatory or feedback mode in conjunction with neuromuscular training. Such interactions between external stimuli and neuromuscular training specifically are lacking in the prior art.

The present invention can be used to address and prevent a wide range of joint related diseases and injuries, such as but not limited to osteoarthritis and ankle sprains. The present invention is not limited to preventing joint-related diseases and injuries in the lower extremity. There is a also a need to be able to provide controlled perturbations to portions of the body other than those in the lower extremity. For example, there is a need to be able to deliver controlled perturbations to areas of the upper body, such as the elbow, wrist or shoulder for the prevention of disease and injury to those regions.

In view of the foregoing, there is a need for a system that can accurately simulate a slip or tripping incident. There is a need for a system that can measure the biomechanics of a slip or tripping incident to further assist a person to better respond to the incident to avoid a fall. There is a further need for an apparatus that is well-suited to measure such biomechanics. There is a need for an apparatus that can simulate various trip and slip scenarios that could lead to a fall so an appropriate response can be developed. There is a need for an apparatus and system that can better train a person to avoid a fall following a trip or slip incident. Moreover, there is a need for a method for fall prevention training to better prepare a person for a disturbance event, including, a slip, trip or fall, to avoid injury or death.

In view of the foregoing, there is a need for a system that can provide task-specific, neuromuscular, dynamic perturbation training to prevent injury to the soft tissues surrounding body joints There is a need for a system that provides perturbations that induce joint instability that requires a neuromuscular response to retain, maintain or retrain intrinsic body joint stabilization There is a need for a system that provides task-specific, neuromuscular, dynamic perturbation training to prevent the development and progression of osteoarthritis and other joint-related diseases. There is a need for a system to provide perturbations during the stance phase of the gait cycle during locomotion. There is a need for a system to provide perturbations during the different phases of stance in the gait cycle to elicit a specific joint response. There is a need for a system to provide perturbations that are controlled and triggered by detecting the braking, midstance and propulsion phases of control for a given joint. There is a need for a system to provide perturbations to a joint at a preferred kinematic position, velocity, or loading condition to elicit and train a specific joint response. There is a need for a system to provide modulation of the stretch reflex to prevent ankle sprains. There is a need for a system that detects the different phases of the gait cycle, including but not limited to the stance phase, which also includes the braking, midstance, and propulsion phase, and which provides a trigger for delivering the perturbation. There is a need for a system that provides aperiodic perturbations to challenge and train the joint response to perturbations that occur during daily living or during sporting activity. There is a need for a system to provide perturbations during athlete training or physical therapy where the perturbations are delivered automatically, and in some cases repeatedly, without any manual intervention from another individual or medical provider.

There is a need for a system that can provide controlled perturbations to any part of the body, including the elbow, wrist and shoulder to help train response to such perturbations and prevent disease and injury to those regions. There is a need for a system that can deliver perturbations very quickly and in an automated and controlled fashion to any part, portion or region of the body.

There is a need for a system to provide perturbations during the stance phase of the gait cycle that are synchronized with musical cues and other external stimulii. There is a further need for a system to provide perturbations of varying magnitude, direction and duration that are generated automatically based on the timing of music driving the system. There is a need for a system that selects music to be presented to a user based on the perturbation profile selected for a given neuromuscular training activity There is a need for a system to provide perturbations that stimulates and trains braking and propulsion control for the joint.

SUMMARY OF THE INVENTION

The present invention preserves the advantages of prior art fall prevention training systems and methods associated therewith. In addition, it provides new advantages not found in currently available fall prevention training systems and methods and overcomes many disadvantages of such currently available systems and methods. In addition, it provides new advantages not found in current injury prevention and neuromuscular training systems and methods and overcomes many disadvantages of such currently available systems and methods.

In accordance with the present invention, a new apparatus and system is provided that studies and analyzes the biomechanics of a disturbance event, such as a slip or trip incident or other disturbance to a part of the body, so that an appropriate response can be executed by the person to reduce or eliminate the number of falls or injury to the body part experienced both in real life and in the simulation/disturbance event. With this new apparatus, system and method, a new and novel method for fall and injury prevention training can be delivered which is superior to training methods known in the prior art.

The present invention uses a new and unique disturbance event simulation apparatus. The apparatus, in accordance with the present invention, may be in the form of a perturbation platform is provided which is movable to create a disturbance event that induces a response from an individual. Sensors are located proximate to the individual and the platform with data being outputted from the sensors. A device is provided for collecting and storing the data during the disturbance event. There is also a device for outputting the data so that it may be viewed and studied. The apparatus may also be a device, such as one that is mounted to a wall, that delivers a perturbation to a part of the person's body, such as a wrist, elbow and shoulder.

Preferably, the perturbation device, such as a platform, is movable to create the disturbance event in less than 500 ms and more preferably in the range of about 100 ms to about 200 ms. In the platform example, it is also preferably a bi-directional motorized belt. Still further, two bi-directional belts can be provided in this embodiment. Also, the apparatus is capable of introducing an obstacle positioned proximate to the platform to induce the response from the individual to the disturbance event. The obstacle, for example, can be a light beam, a three-dimensional object or a hologram.

In accordance with the present invention regarding delivering a disturbance event to a person in a walking gait, an embodiment in provided with a new apparatus and method that monitors the phase of the gait cycle for an individual standing or ambulating on the apparatus and which actuates the biomechanics of a disturbance event, so that an appropriate response can be executed by the person to improve measurable quantities such as dynamic stability or improved neuromuscular response that have been linked to ACL injury, OA, and joint instabilities. With this new apparatus, system and method, a new and novel method for dynamic neuromuscular training can be delivered which is superior to training methods known in the prior art. The current invention improves on the existing systems by delivering systematic, progressive perturbations while, if desired, simultaneously recording relevant training data. The perturbations may be timed to events in the gait cycle, such as but not limited to heelstrike or toeoff. The perturbations may be programmed to occur on every occurrence of such a gait cycle event, or at multiples of such a gait cycle event, or at a random number of occurrences of such a gait cycle event, Additionally, the perturbations may occur randomly but not during a specific gait cycle event.

The current invention provides a system for perturbations that induce joint instability in one or more body joints, individually or simultaneously, and not limited to lower extremity. This can include the spine. When the perturbation is provided to the lower extremity, the timing of the perturbation within the gait cycle at which the perturbation is induced and the magnitude of the perturbation may affect body joints in different ways, including both the magnitude and activation patterns of the musculature around the joints, and subsequently the response of the body, such as ankle flexion, knee flexion, hip flexion, trunk flexion, or a step response.

The present invention can also be modified to address joints that are not in the lower extremity or associated directly with walking and fall prevention. The present invention is envisioned to include an embodiment where a perturbation device is provided, such as mounted to a wall for example, that delivers a perturbation to a part of the body that is not in the lower extremity, such as the wrist, elbow or shoulder. The person may reach out and grasp a handle and perform a certain exercise or movement. Then, at a desired point or points during the motion, a perturbation is delivered in less than 500 ms to the joint involved in the exercise for recordal of results for subsequent training purposes.

This unique apparatus can be employed to carry out the new and novel method of disturbance event training of the present invention, which includes fall prevention and other joint movement training.

For the fall prevention training aspect of the present invention, it is preferred that the following steps are provided as part of a unique protocol, however, less than all of the steps may be employed and still be within the scope of the present invention. Using the platform of the present invention, from a stop, a sequence of disturbance events are produced with incrementally increasing perturbation distance that establishes a first threshold of that individual's "foot in place" response and not a step response.

Next, from a stop, a sequence of disturbance events are produced with incrementally increasing perturbation distance that establishes a second threshold beyond which the individual can not execute a single step response.

Next, a first obstacle, having a first obstacle height, is placed proximate to the platform at a first obstacle distance to induce the step response of the individual to the disturbance event. From a stop, a sequence of disturbance events are produced with incrementally increasing perturbation distance that establishes a third threshold beyond which the individual can not execute a single step response while attempting to negotiate the obstacle. Further, from a stop, a sequence of the combination of a disturbance event with incrementally increasing perturbation distance are produced followed by a continuous platform motion simulating walking velocity that establishes a fourth threshold beyond which the individual can not achieve a stable gait response.

Next, from a stop, a stable gait response is sought from the individual. If they are able to achieve a stable gait within a predetermined number of steps, the trial is considered successful. If the individual requires more than the predetermined number of steps to achieve stable gait or if the individual falls, the change in velocity is repeated. Trials are be repeated within a session or across sessions until the variability in step response following a given perturbation displacement and profile are below a target value.

Next, a second obstacle, having a second obstacle height, is placed proximate to the platform at a second obstacle distance to induce the step response of the individual to the disturbance event. From a stop, a sequence of a combination of a disturbance event with incrementally increasing perturbation distance is produced followed by a continuous platform motion simulating walking velocity that establishes a fifth threshold beyond which the individual can not achieve a stable gait response. Further, from a first walking velocity created by a continuous platform motion, a sequence of the combination of a disturbance event with incrementally increasing perturbation distance is produced followed by a continuous platform motion returning to the first walking velocity that establishes a sixth threshold beyond which the individual can not achieve a stable gait response.

Next, the individual starts at an initial steady state locomotion velocity with a large disturbance introduced at a random time. The disturbance causes the platform to accelerate to a prescribed disturbance velocity before returning to a second steady state locomotion velocity. The maximum time for this change in the platform velocity is less than about 500 ms, and is more typically in the range of about 100 to about 200 ms. A stable gait response is sought from the individual.

Finally, a third obstacle, having a third obstacle height, is placed proximate to the platform at a third obstacle distance to induce the step response of the individual to the disturbance event. From a second walking velocity created by a continuous platform motion, a sequence of the combination of a disturbance event with incrementally increasing perturbation distance is produced followed by a continuous platform motion returning to the second walking velocity that establishes a seventh threshold beyond which the individual can not achieve a stable gait response.

It is therefore an object of the present invention to provide a new and novel apparatus for use with fall prevention training that more accurately simulates a disturbance event, such as a slip or trip incident, more closely than prior art apparatus.

It is another object of the present invention to provide an apparatus and system that can measure the biomechanics of a disturbance event to further assist a person to better respond to the incident to avoid a fall.

Another object of the invention is to provide an apparatus that is well-suited to measure such biomechanics.

An object of the invention is to provide an apparatus that can simulate various disturbance events that could lead to a fall so an appropriate response can be developed.

A further object of the present invention is to provide a new and novel method for fall prevention training that train a person to avoid a fall when encountered with a disturbance event.

Another object of the present invention is to provide a method for fall prevention training that better prepares an individual for a disturbance event to avoid injury or death.

Yet another object of the present invention is to provide a method for fall prevention training that has a protocol that effectively trains the individual while isolating the weaknesses of the individual.

An object of the current invention is to provide task-specific, neuromuscular, dynamic perturbation training to prevent injury to the anterior cruciate ligament (ACL) and other soft tissues in the joints of the lower limb and to improve outcomes for athletes who sustain these injuries, either with or without subsequent surgery to repair or replace the injured ligament or ligaments. Previous research has demonstrated that manual perturbation training has been shown to improve outcomes for both ACL-deficient (ACL-D) and ACL-reconstructed (ACL-R) populations compared to the strength training alone.

An object of the current invention is to provide perturbations that induce joint instability that requires a neuromuscular response to retain and maintain balance, joint stability, and joint response time to disturbances The joint instability can occur at a single joint, simultaneously at multiple joints throughout the body, or at time-delayed periods at different joints. The instability requires a response, such as a step response or other, anything from the movement of one or more joints to actually physically changing the body's base of support (moving the foot or feet) to maintain balance. The joint(s) affected by the perturbation are a function of the timing in the gait cycle, the body position and body motion (e.g. defined as the motion of the center of mass, or the motion of independent limbs, and the like) at the time of the perturbation, and the magnitude of the perturbation delivered. Any joint in the body can be affected by this.

An object of the current invention is to provide perturbations that induce joint instability that requires a neuromuscular response to retain and maintain balance, joint stability, and joint response time to disturbances The joint instability can occur at a single joint, simultaneously at multiple joints throughout the body, or at time-delayed periods at different joints. The instability requires a response, such as a step response or other, anything from the movement of one or more joints to actually physically changing the body's base of support (moving the foot or feet) to maintain balance. The joint(s) affected by the perturbation are a function of the timing in the gait cycle, the body position and body motion (e.g. defined as the motion of the center of mass, or the motion of independent limbs, and the like) at the time of the perturbation, and the magnitude of the perturbation delivered. Any joint in the body can be affected by this. Perturbations can be delivered to any joint in the body, whether or not it is in the lower or upper extremity of the body and whether or not the joint is associated with the act of walking.

Another object of the current invention is to provide task-specific, neuromuscular, dynamic perturbation training to prevent the development and progression of osteoarthritis.

Another object of the current invention is to provide perturbations, such as those that are continuous or periodic or aperiodic, during the different phases of stance of the gait cycle.

Another object of the current invention is to provide perturbations, such as those that are continuous or periodic or aperiodic, during each stance phase of the gait cycle.

Another object of the current invention is to provide modulation of the stretch reflex to prevent ankle sprains.

Another object of the current invention is to provide perturbations during the athlete training or physical therapy where the perturbations are delivered automatically without any manual intervention from another individual or medical provider.

Another object of the current invention is to provide perturbations during the stance phase of the gait cycle that are synchronized with musical cues or other external stimuli, including but not limited to visual, auditory and tactile stimuli.

A further object of the present invention is to provide perturbations to any joint of the body to help prevent disease and injury thereto.

Another object of the current invention is to provide perturbations of varying magnitude, direction and duration that are generated automatically based on the timing of music driving the system. Another object of the current invention is to provide selection of music or other external cues to be presented to a user based on the perturbation profile selected for a given neuromuscular training activity Another object of the current invention is to provide perturbations that are based on the timing of braking and propulsions of a joint.

BRIEF DESCRIPTION OF THE DRAWINGS

The novel features which are characteristic of the present invention are set forth in the appended claims. However, the invention's preferred embodiments, together with further objects and attendant advantages, will be best understood by reference to the following detailed description taken in connection with the accompanying drawings in which:

FIG. 15A is an exploded front view of a lateral deck to provide lateral perturbations controlled by a DC rack-and-pinion drive centered under the deck and slides on a low friction polymer surface that is fixed to an aluminum sub-frame;

FIG. 15B is perspective view of a lateral deck shown in FIG. 15A with the sub-frame;

FIGS. 19A-D illustrate various graphs of multi-step data relating to operation of the motor of a perturbation platform in accordance with the present invention;

DETAILED DESCRIPTION OF THE PREFERRED EMBODIMENT

Figure 7:
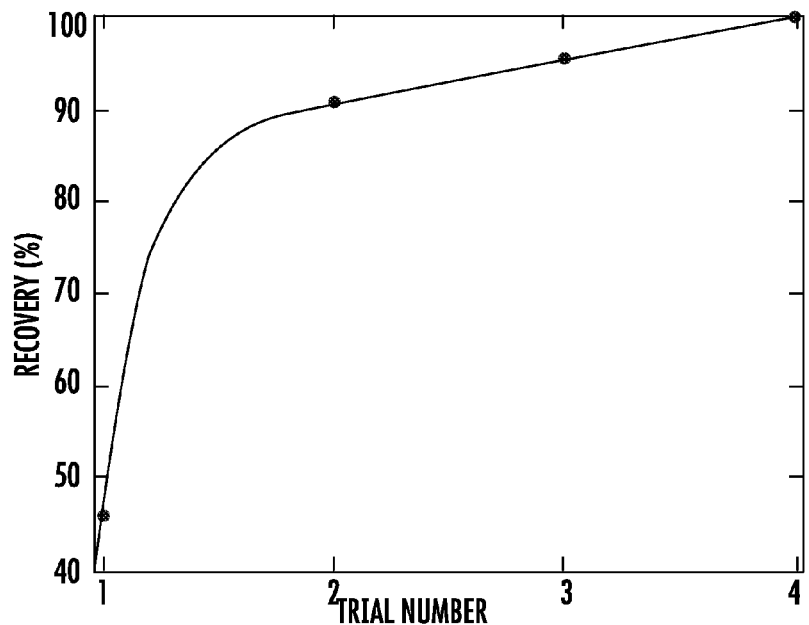
FIG. 7 is a graph showing the increase in recovery percentage in individuals over time as a result of fall prevention training.

The present invention includes a unique method that enables individuals, particularly older adults, to rapidly learn how to modify motor performance and improve recovery rates after being subjected to a disturbance event or perturbation that required a response, such as a step response. The method of the present invention achieves a reduction in the probably of falling by repeated exposure to a realistic disturbance event which serves as targeted and effective motor skill training. As seen in FIG. 7, the recovery percentage increases exponentially over time when they are subjected to trials of fall prevention training. Thus, the method of the present invention provides an invaluable rehabilitation tool for an individual for training how to recover from a large disturbance event, such as a large postural perturbation. To carry out this method, the present invention employs a cost-effective apparatus that can be widely used to reduce the incidence of falling.

The present invention includes a new and novel apparatus and a method which can use that apparatus for fall prevention training. It should be understood that it is preferred that the apparatus of the present invention be used to carry out the method of the present invention. However, the method of the present invention can be carried out by a many different types of training apparatus and still be within the scope of the present invention. The preferred embodiment of the apparatus in accordance with the present invention is set forth in detail below in connection with FIGS. 1-6.

Figure 1:
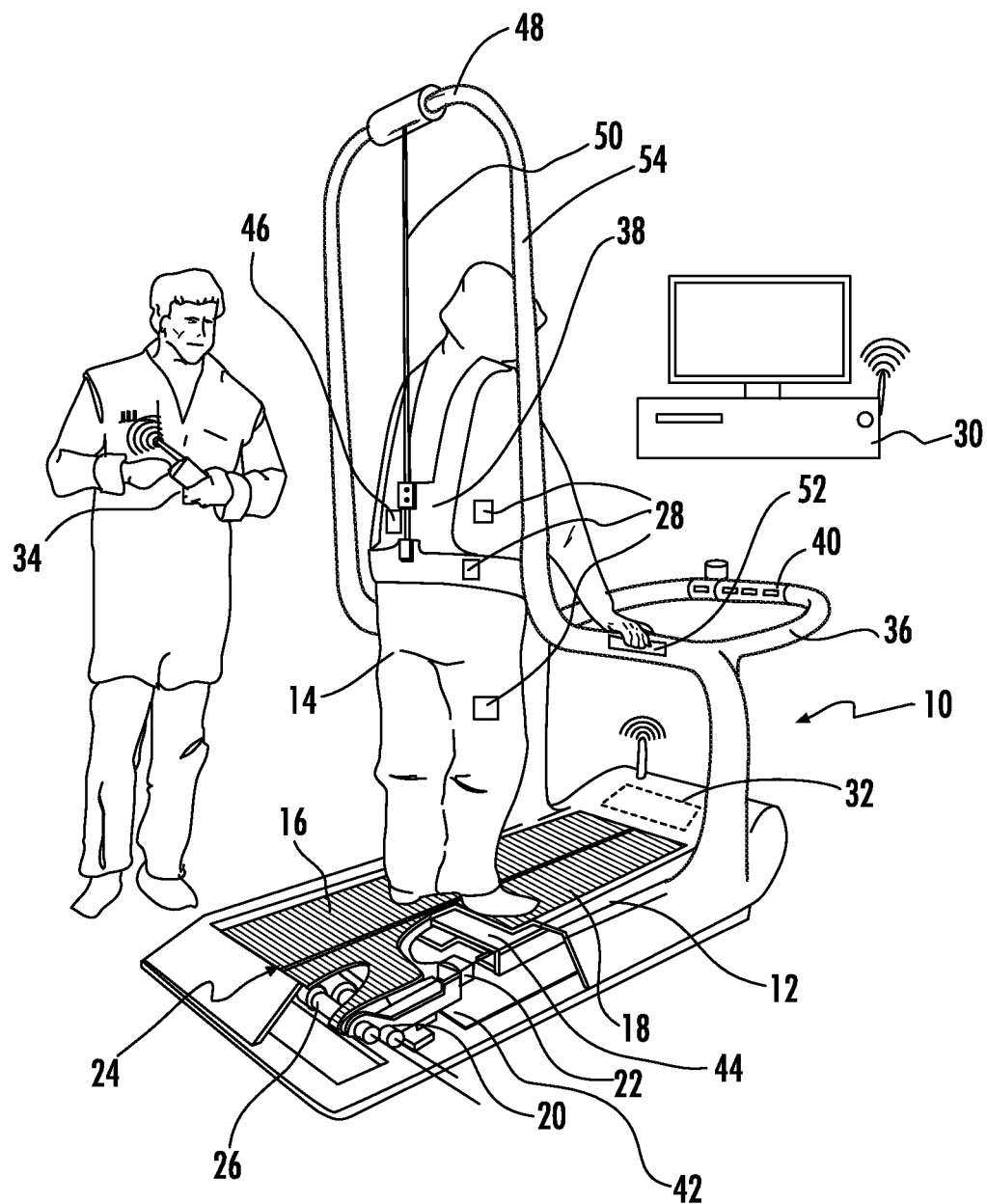
FIG. 1 is a perspective view of the apparatus of the present invention.

Referring first to FIG. 1, an apparatus 10 for use in carrying out the method of the present invention is provided. Preferably, the apparatus 10 is in the form of a force-treadmill perturbation treadmill 12, as shown in FIG. 1, for use in identifying individual risk factors for falling in an individual 14. The following details of the apparatus 10 are preferred to carry out the method. However, it should be understood that many other different types of apparatus 10 can be employed and the components therein can be modified to suit the application at hand. All of these modifications are deemed to be within the scope of the present invention.

The treadmill 12 includes a left belt 16 and a right belt 18, which are both preferably bi-directional for maximum control and timing of belt position, velocity and acceleration. For example, each belt 16, 18 preferably has bi-directional displacement control for large perturbations from 6 mm (0.25 in) to infinity (continuous operation) with minimum 6 mm (0.25 in) resolution. The belts 16, 18 also have bi-directional velocity control from 0-4 m/s (~9 mph) and bi-directional acceleration control from 0-6 m/s$^2$. The belts 16, 18 are critically tuned to avoid oscillations. As far as preferred dimensions, each belt 16, 18 is approximately 250 mm (~10 in) wide with a platform length of approximately 1.6 m (5 ft). It is also possible that a single belt (not shown) may be used instead of the dual belts 16, 18 shown in FIG. 1.

The apparatus 10 also includes a motor and drive system 20. A high torque direct drive motor is preferred although other drive systems 20 may be used. Motors for driving belts are well known in the art and need not be discussed further therein.

Most importantly, the apparatus 10 is configured to create the disturbance event in less than 500 ms. More preferably, the disturbance event is created in the range of about 100 to about 200 ms. The creation of the disturbance event, such a movement of a belt 16 or 18, at such a fast speed is not found in the prior art. The relatively short duration of the disturbance event is used so that it simulates a real disturbance event to trigger a more accurate response from the individual 14.

Figure 6:
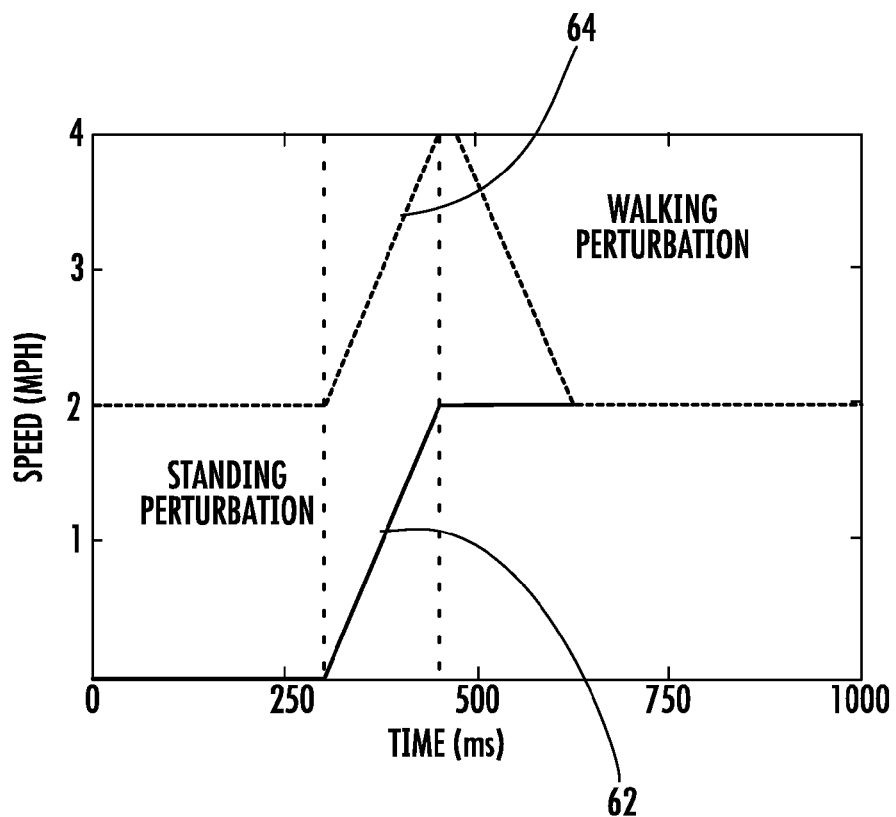
FIG. 6 is a graph showing speed against time for executing a standing and walking perturbation in accordance with the present invention.

FIG. 6 is a graph of the speed of a belt 16, 18 against time to illustrate the unique fast creation of a disturbance event. Line 62 represents the speed of creation of a disturbance event for a standing perturbation where the individual 14 is standing still and belts 16, 18 are ramped up to a 2 MPH speed in the range of about 100 to about 200 ms. Similarly, line 64 Line 64 represents the speed of creation of a disturbance event for a walking perturbation where the individual 14 is walking at about 2 MPH and belts 16, 18 are accelerated over 4 MPH in the range of about 100 to about 200 ms.

Further, multi-axis load transducers 22, such as low-profile multi-axis load cells with desired range, accuracy, and sensitivity, which support the platform, generally referred to as 24 of treadmill 12, and drums 26 of the treadmill apparatus 12. The pressure applied by an individual 14 to the bed of the platform 24 can be measured with such pressure transducers 22.

Figure 5:
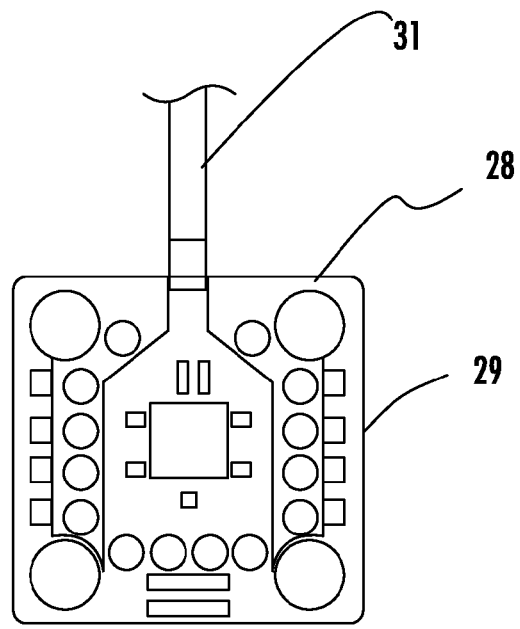
FIG. 5 is a top plan view of an inertial sensor used in the present invention.

The apparatus 10 of the present invention also includes a number of sensors 28 that are attached the individual 14 that is being trained and optionally at various locations on the apparatus 10 itself. For example, inertial sensors 28, which are well known in the art, can be placed on various parts of the body of the individual 14 to sense position and velocity. An example of a prior art inertial sensor 28 is shown in FIG. 5 with circuit board 29 and electrical lead 31. As a further example, an inertial sensor 28 can be positioned on the trunk of the individual 14 to sense trunk angle and velocity, which are important factors to be studied in connection with fall prevention training. While sensors 28 are preferred, other ways to measure body location can be used, such as video analysis of body movement.

Sensors located between the underside of the belts and the deck of the apparatus sense the location of the subject's foot as it contacts the platform. This plurality of sensors is preferably in an array with a sensing element every 1 cm in both the length and width direction of the apparatus. In the preferred embodiment, these sensing elements are made, for example, from a thin pressure sensitive material and are contact sensors whose electrical output is triggered when foot contact pressure to the sensor through the belt exceeds a certain pre-determined level. While this array of thin contact sensing elements is the preferred embodiment, these sensing elements could also produce a voltage whose output was proportional to applied pressure or force. Also, while thin pressure sensitive material is preferred, any type of sensors, which can be either of the digital ON/OFF or proportional analog, can also be used in accordance with the present invention.

The sensors 28 gather data regarding the various parameters that are being monitored. This data is, preferably in real-time, sent to a computer 30 for processing and analysis. The data may be sent to the computer 30 wirelessly or by hard wire. Data transmission and computer processing devices are so well known in the art that they need not be discussed in further detail herein.

The apparatus 10 itself preferably includes its own central control unit 32 with the appropriate control algorithm and custom motor control software, which provides bilateral, independent bi-directional real-time biofeedback motor control function. The control algorithm is written as a state machine, and responds according to a lookup-table of inputs to determine the next step. A radio frequency (RF) telemetry console 34 is used for many operational functions of the apparatus 10, including programming and operation of handrails 36, safety harness 38, and emergency stop switch 40. The control algorithm is preferably written in C using LabWindows CVI software and, where appropriate, native microcontroller firmware language. The key elements of the control system 32 include encoders attached to drive motors provide data for motion control of the platform 24 and PID algorithms for smooth, accurate motion. Also, the control system handles triggering of perturbations at specific times during the walking cycle based on force measurements and monitoring and recording of step recovery response and appropriate state-machine response to inputs. There are also safety interlocks to protect the individual 14. Thus, the treadmill apparatus 10 of the present invention includes two main components, the perturbation platform (PPU) 24 with force measurement capability, safety harness 38 and handrails 36 as well as a central control unit (CCU) 32 with control algorithms, safety interlocks, data storage and transfer protocols, and user interface.

Referring back to FIG. 1, the treadmill apparatus 10 includes a frame 42 to integrate the platforms on the underside of each transducer and provide rigid attachment points for the mounting of the treadmill 10 to the ground. The frame 42 is designed to minimize any mechanical crosstalk that may be induced by the use of a common frame. The belts 16, 18 and platforms 44 thereunder are separated by a physical width of 0.125 in. to minimize any influence two separate belts 16, 18 may have on gait patterns of the individual 14 during walking while preventing any belt overlap that may occur.

The apparatus 10, which includes a motor controller and amplifier with associated electronics within the CCU 32, is preferably PC based with cabling to the amplifiers to enable a development environment for testing.

The apparatus 10, as seen in FIG. 1, also includes a harness system 38 that embraces the individual 14 and is suspended from support bar 48 via tether 50. Support bar 48 is positioned by vertical posts 54. Force transducers 46, mounted in the training harness 38, generate use input signals to determine when an individual 14 has fallen. The harness 38 is used as both a safety subsystem and as a control input device to system software, and is integrally attached to the platform 24 through the subsystem frame. Known chest harnesses (e.g. climbing chest harness) are integrated to the subsystem frame using tubular steel. Further, low-profile handrails 36 are included as a safety feature. The handrails 36 are attached to the treadmill 12 base in such a way that the force transducers 52 can identify and quantify when the rails 36 are being used to support the individual's body weight. This data is also used for real-time biofeedback control of the treadmill 12. Powder coated bent tubular steel and powder coated for each rail 36, 54 is preferred although other handrail constructions may be used.

Software modules are an important component of the apparatus and control thereof of the present invention. Software modules are preferably developed in a high level language, such a C, but are designed for implementation on an embedded microcontroller or dedicated microprocessor. Computational modules are also employed for kinematic measurements derived from numerous markers placed on the body for computations of stepping response to large postural perturbations. For example, 26 markers on the body of the individual 14 may be used. These measures, including trunk angle and trunk velocity, are of assistance to discriminate fallers versus non-fallers.

It should be understood that each of the foregoing components are preferably included in the apparatus 10 of the present invention. However some components and features may be omitted from the apparatus and still be within the scope of the present invention. For example, the apparatus 10 employs force transducers 44, 46, 54, however, such force measurements may not be required for the analysis of the kinetic data in order to be effective as a training tool. For example, it may be sufficient to have programmed control algorithms and relatively simple sensing capabilities that perform universal protocols.

Figure 2:
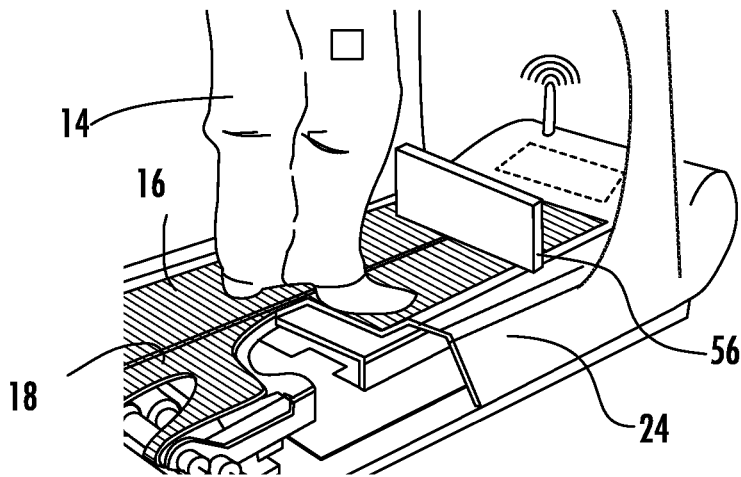
FIG. 2 is a close-up perspective view of the apparatus of the present invention equipped with a physical obstacle.
Figure 3:
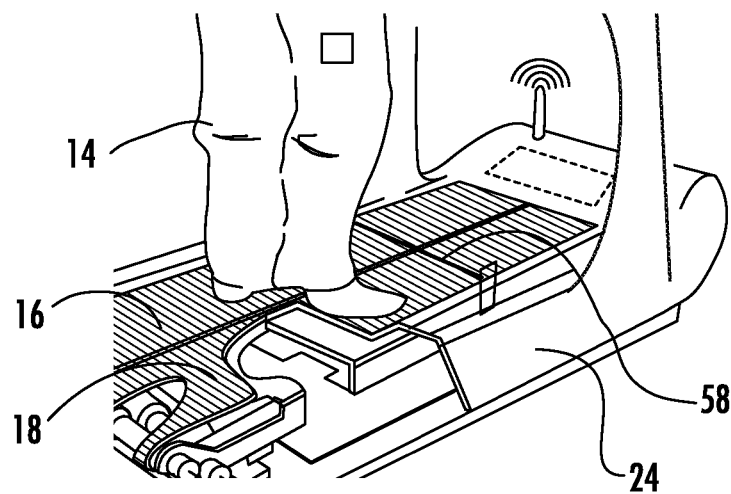
FIG. 3 is a close-up perspective view of the apparatus of the present invention equipped with a virtual obstacle in the form of a laser beam.
Figure 4:
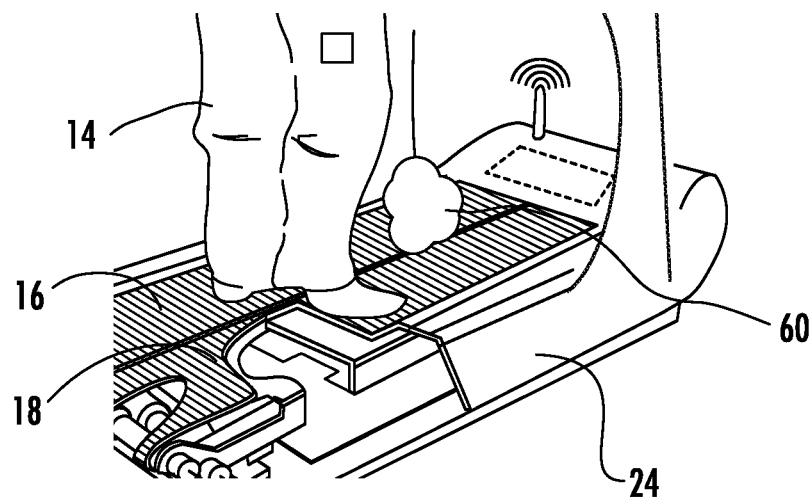
FIG. 4 is a close-up perspective view of the apparatus of the present invention equipped with a virtual obstacle in the form of a hologram.

Referring now to FIGS. 2-4, the optional use of obstacles with the apparatus 10 of the present invention. The use of such obstacles in the method of training of the present invention improves the overall effectiveness thereof. In FIG. 2, the treadmill 24 is equipped with a physical obstacle 56 that is placed proximate to the individual. For example, the obstacle 56 is a wall or barrier that is place in front of the walking path of the individual 14. This obstacle 56 may be place above the belts 16, 18 or may be placed directly thereon. Or, the obstacle 56 may, upon command, emanate upwardly from the platform 24 to then be proximate to the individual 14.

In FIG. 3, the obstacle employed, in this embodiment, is a laser beam 58 that passes proximate to the individual 14, namely, in their walking path. Still further, in FIG. 4, the obstacle employed, in this embodiment, is a hologram 60. As will be discussed below, in connection with the method of the present invention, the obstacles 56, 58 and 60 play an important role in training the individual 14. The obstacles 56, 58 and 60 simulate real obstacles that may be faced in a real world non-training setting. The virtual obstacles 58 and 60 may also be used to sense when the individual 14 passes therethrough to serve as an additional sensor.

In view of the foregoing, the apparatus 10 of the present invention can measure an individual's step response to a disturbance event, such as trip or slip incident. Therefore, it can be used to evaluate tripping and slipping fall mechanism in anterior and posterior directions. It can also evaluate stepping responses from static positions in the anterior, posterior and lateral directions. Recovery strategies can also be evaluated to reduce occurrences of falls. The complete measurement and computational capabilities of the present invention enables specific individual risk factors to be identified so appropriate training can be developed and carried out to better avoid fall incidents. Thus, novel biomechanical factors can be linked to the prediction and prevention of falling with better accuracy and effectiveness than prior art devices and systems.

The data obtained from the system and apparatus of the present invention can then be used to better train a person for a fall in accordance with the new method for fall prevention training of the present invention. As discussed in detail below, the apparatus 10 can be used to execute a unique protocol of fall prevention training that teaches a person how to better react to a disturbance event according to strategies learned from the apparatus and system described above. For example, a succession of simulated trip incidents can be delivered where the velocities and/or accelerations or a combination thereof of each successive event is built up over time to lead up to a trip situation. By using the unique apparatus 10 of the present invention, a method of training can be delivered where a slip incident can be generated from a static position. This simulates a condition where an individual loses their balance when standing still.

Also, and most importantly, the present invention can generate a dynamic slip or trip condition where a second velocity is delivery after a first velocity has been delivered. This simulates a condition where the individual is walking (corresponding to the first velocity) and then encounters a trip or slip situation while walking Thus, a change of velocities can be delivered to better simulate various conditions that cannot be simulated with prior art devices. Such a method of training is preferably carried out using the apparatus of the present invention described above.

Referring now to FIGS. 8-14, details of the method of fall prevention training is shown and described in detail. The method of the present invention provides a protocol to execute and carry out the fall prevention training of the present invention. This is a general protocol employed in the method of the present invention and can be applied to any of the large disturbance events used in the present method of training. As will be discussed in detail below, the method is a multi-stage process that outlines a unique training progression that is used in an attempt to reduce the incidence of falls by an individual. While this is a preferred method, there is no set number of cycles or limits. In general, the method uses a unique protocol that requires the individual to achieve a goal to represent the acquisition of a given skill. Moreover, multiple trials at a given disturbance level represents skill retention and the results of future retesting indicates skill decay.

Stage 1—Small Disturbance, No Step Response

Figure 8:
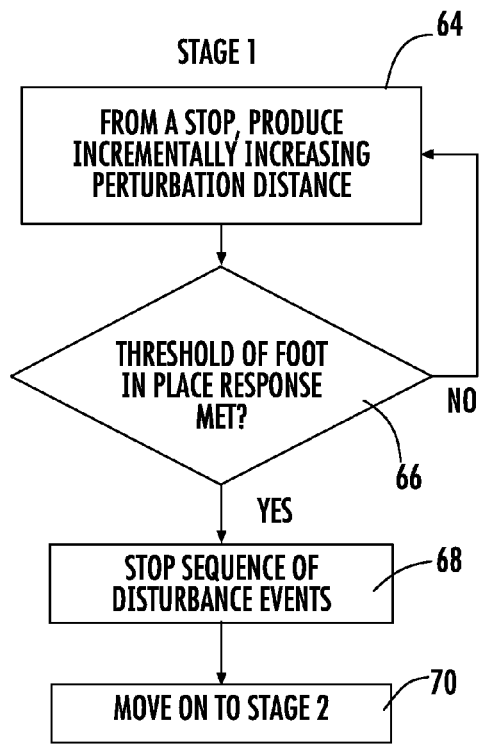
FIG. 8 is a flow chart illustrating the execution of Stage 1 of the method of the present invention.

As represented by FIG. 8, in the first stage of the protocol, the individual 14 stands with two feet on platform. A small disturbance is introduced at a random time. The platform moves a finite distance and stops. As stated above, the platform moves in less than about 500 ms and, preferably, in the range of about 100 ms to about 200 ms to ensure a realistic disturbance event. The disturbance level in Stage 1 should be small to determine if the individual can use respond to the disturbance with what is commonly referred to as a "feet in place" recovery strategy. This means that the individual adopts a recovery strategy that maintains upright posture and which requires minimal movement of the feet (e.g. no step response).

For example, the individual might use what is referred to as an "ankle strategy" or a "hip strategy" whereby the individual alters their ankle and/or hip rotation angle in one or more directions and stabilizes their body with their muscles with no step response. At this stage, the perturbation distance preferably remains the same until the individual has shown that their response is low in variability.

The perturbation distance incrementally increases at 64 as the individual successfully completes the feet in-place response. This increase in distance continues until the individual is able to complete a prescribed distance, or threshold, which is determined based on intrinsic parameters of the individual, such as height, body center of mass, age, and flexibility. Once the individual has exceeded the predetermined maximum perturbation threshold without a step response at 66, the sequence of disturbance events are stopped at 68 and they are moved to the Stage 2 in the protocol at 70.

Stage 2—Step Response to Large Perturbation

Figure 9:
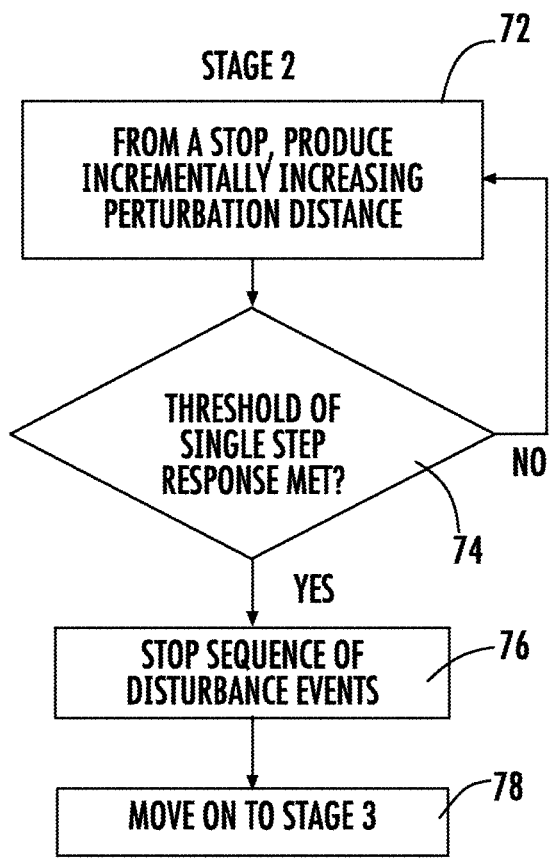
FIG. 9 is a flow chart illustrating the execution of Stage 2 of the method of the present invention.

In FIG. 9, the individual starts at a standstill and a large disturbance is introduced at a random time. The platform moves a finite distance and stops. The disturbance magnitude preferably exceeds the magnitude of the maximum disturbance in Stage 1 above. The maximum time for this displacement of the disturbance to occur is less than 500 ms, and is more typically in the range of about 100 to about 200 ms, and preferably about 250 ms.

In Stage 2, a single step response by the individual is sought. If the individual is able to maintain posture with a single step, the given train within Stage 2 is considered successful. If the individual requires more than one step to maintain posture or falls, the perturbation distance is repeated.

Trials are be repeated within a session or across sessions until the variability in step response following a given perturbation displacement and profile are below a target value. For example, a minimization function relating step length and step width might be employed to calculate a residual value for step response. This value is called a target step response. The variance in this computed value for a given trial compared to the previous n trials can be used. Alternative methods of determining a threshold for success for step response to a given perturbation are readily defined, such as the number of trials in a row for achieving the target step response required by Stage 2.

After an individual successfully passes the single step response test for a given perturbation distance and acceptably low variability between sessions, that distance is increased at 72 until individual is able to complete a prescribed perturbation distance threshold at 74. In similar fashion to Stage 1, intrinsic parameters of the individual, such as height, body center of mass, age, and flexibility, are used to determine a maximum perturbation distance, or threshold, for that individual. Once the individual has exceeded the predetermined maximum perturbation with only a single step response, the sequence of disturbance events are stopped at 76 and they are moved to the Stage 3 in the protocol of the method of the present invention at 78.

Stage 3—Step Response with First Obstacle

Figure 10:
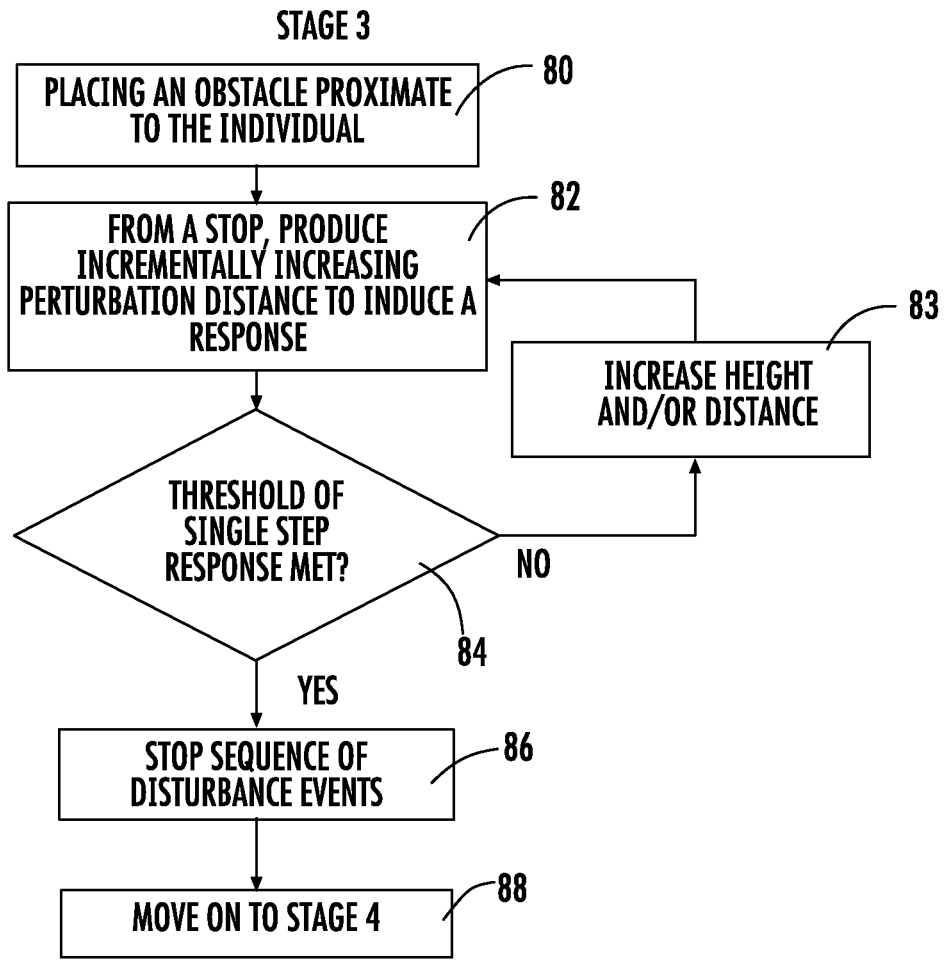
FIG. 10 is a flow chart illustrating the execution of Stage 3 of the method of the present invention.

In FIG. 10, the individual starts at a standstill. A first obstacle is placed proximate to the individual at 80, such as ahead of the individual in the direction, so that the perturbation forces them to make a step response. A large disturbance is also introduced at a random time. The platform moves a finite distance and stops. The disturbance magnitude exceeds the magnitude of the maximum disturbance in Stage 1. The maximum time for this displacement of the disturbance to occur is less than about 500 ms, and is more typically in the range of about 100 to about 200 ms.

The distance and position that the first obstacle is placed from the individual can vary between zero (i.e. touching the individual) and a prescribed maximum obstacle distance from individual. Intrinsic individual parameters, such as height and body center of mass, are used to determine a maximum obstacle distance from individual for that individual. The obstacle can either be real or virtual. For example, the obstacle, which may be made from any material, may be a barrier or wall that emanates up from the floor of the platform. Such an obstacle may be driven by springs or actuators to control its positioning proximate to the individual. For virtual obstacles, 3-D holograms and laser beam systems are a few examples. In the preferred embodiment of the present invention, the obstacle is 5 cm high but it could be of any height. For example, the obstacle may be in the range of only about 1 mm up to about one half of the body height of the individual.

A single step response is sought from the individual. If they are able to negotiate the obstacle and to maintain posture with a single step, the trial is considered successful. If the individual requires more than one step to maintain posture or falls, the perturbation distance is repeated.

Trials are repeated within a session or across sessions until the variability in step response following a given perturbation displacement and profile are below a target value. For example, a minimization function relating step length and step width might be employed to calculate a residual value for step response. This value is called a target step response. The variance in this computed value for a given trial are compared to the previous n trials can be used. Alternative methods of determining a threshold for success for step response at 84 to a given perturbation are readily defined, such as the number of trials in a row for achieving the target step response.

After a individual successfully passes the single step response test for a given perturbation distance, that distance is incrementally increased at 82 until individual is able to complete a prescribed distance. Also, the height of the obstacle is progressively increased at 83 up to a prescribed height and the initial distance of the obstacle from the individual is progressively increased up to a prescribed perturbation distance.

The intrinsic individual parameters, such as height, body center of mass, age, and flexibility, are used to determine a maximum perturbation distance for that individual, the maximum obstacle height for that individual and the maximum initial obstacle distance for the individual. Once the individual has exceeded the predetermined maximum perturbation, with only a single step response and acceptably low variability between sessions, the disturbance events are stopped at 86 and they are moved to the Stage 4 at 88 in the protocol outlined below. It should be noted that in the case where the disturbance event is intended to be large and to simulate a slip incident, Stage 3 may be omitted.

Stage 4—Stable Gait After Standstill

Figure 11:
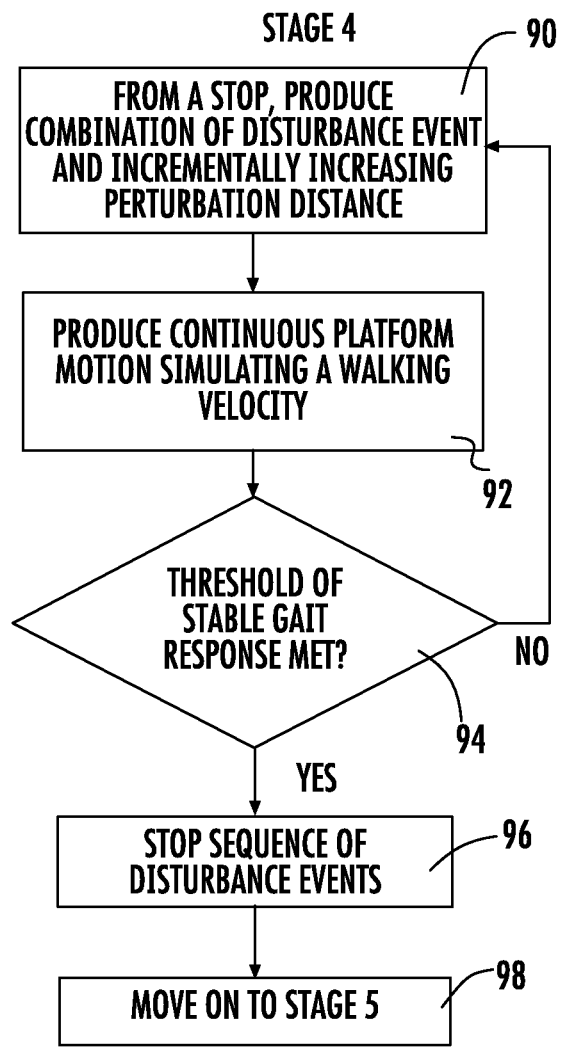
FIG. 11 is a flow chart illustrating the execution of Stage 4 of the method of the present invention.

In FIG. 11, the individual 14 starts at a standstill and a large disturbance is introduced at a random time. The disturbance causes the platform to accelerate to a prescribed (non-zero) velocity. This second velocity is called the velocity change. The maximum time for this change in the platform velocity is less than about 500 ms, and is more typically in the range of about 100 to about 200 ms.

A stable gait response is sought from the individual. If they are able to achieve a stable gait within a predetermined number of steps, the trial is considered successful. If the individual requires more than the predetermined number of steps to achieve stable gait or if the individual falls, the change in velocity is repeated. Trials are be repeated within a session or across sessions until the variability in step response following a given perturbation displacement and profile are below a target value.

For example, a minimization function relating step length and step width might be employed to calculate a residual value for step response. This value is called a target step response. The variance in this computed value for a given trial compared to the previous n trials can be used. Alternative methods of determining a threshold for success for step response to a given perturbation are readily defined, such as the number of trials in a row for achieving the target step response.

After a individual successfully passes the stable gait response test for a given velocity change perturbation, that velocity change is incrementally increased at 90 to produce continuous walking at 92 until individual is able to successfully complete a prescribed velocity change. Intrinsic individual parameters, such as height, body center of mass, age, and flexibility, are used to determine a maximum velocity change threshold at 94 for that individual. Once the individual has exceeded the predetermined maximum velocity change with stable gait step response and acceptably low variability between sessions, the disturbance events are stopped at 96 and they are moved to the Stage 5 in the protocol at 98.

Stage 5—Stable Gait After Standstill With Second Obstacle

Figure 12:
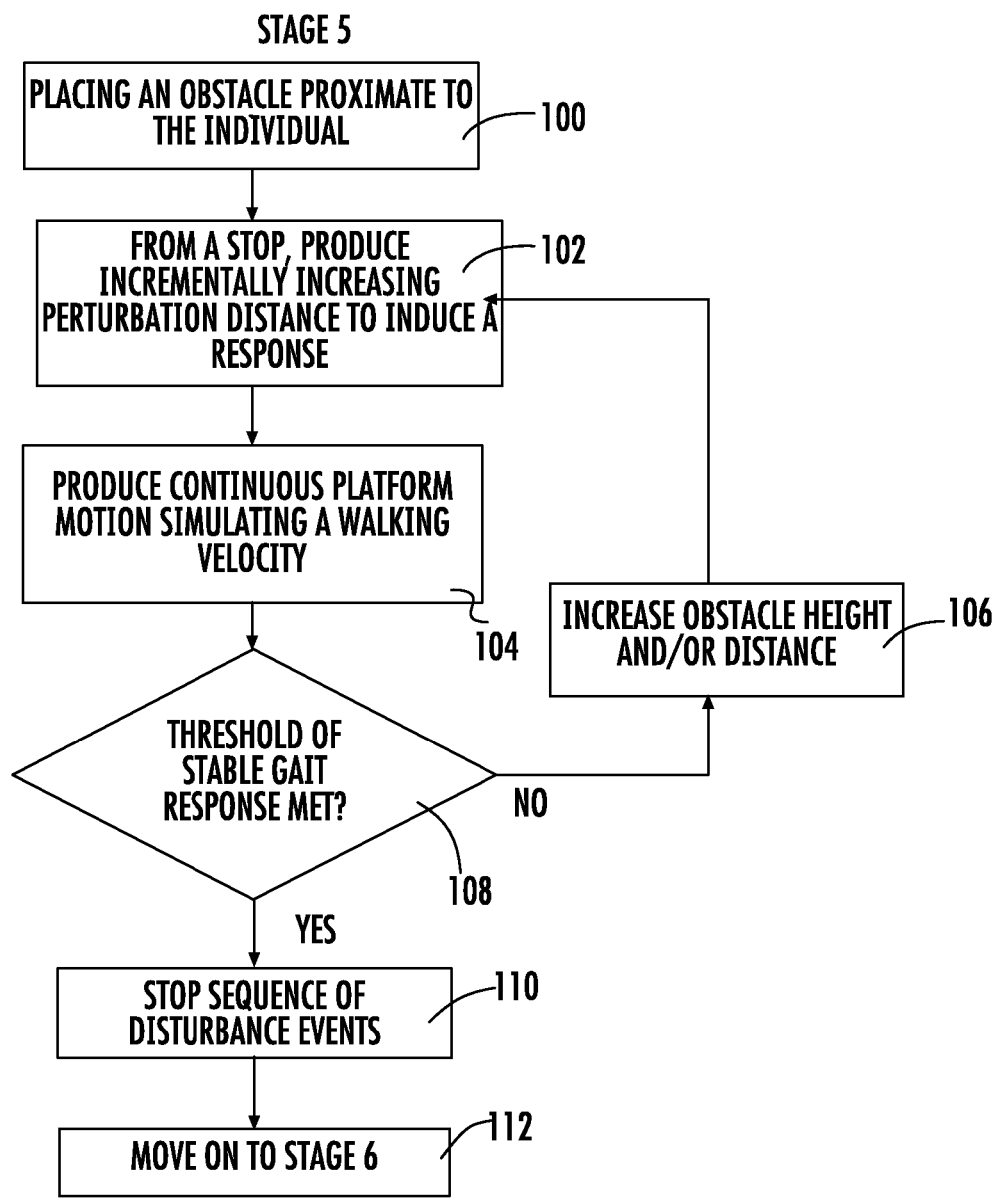
FIG. 12 is a flow chart illustrating the execution of Stage 5 of the method of the present invention.

In FIG. 12, the individual 14 starts at a standstill. A second obstacle is placed proximate to the individual at 100, such as ahead, in the direction such that the perturbation forces them to make a step response. This second obstacle may be the same as the first obstacle but also may be a different obstacle. A large disturbance is introduced at a random time. The disturbance causes the platform to accelerate to a prescribed (non-zero) velocity. This second velocity is called the velocity change. The maximum time for this change in the platform velocity is less than 500 ms, and is more typically in the range of about 100 to about 200 ms.

The distance that the second obstacle is placed from the individual can vary between zero (i.e. touching the individual) and a prescribed maximum obstacle distance from individual. Intrinsic individual parameters, such as height, body center of mass, age, and flexibility are used to determine a maximum obstacle distance or threshold from individual for that individual. As above, the second obstacle can either be real virtual and preferably 5 cm high, although, the obstacle could be in the range of 1 mm up to about one half of the body height of the individual.

A stable gait response is sought in Stage 5. If the individual is able to achieve a stable gait within the predetermined number of steps, the trial is considered successful. If the individual requires more than the predetermined number of steps to achieve stable gait or if the individual falls, the change in velocity is repeated.

Trials are be repeated within a session or across sessions until the variability in step response following a given perturbation displacement and profile are below a target or threshold value. For example, a minimization function relating step length and step width may be employed to calculate a residual value for step response. This value is be called a target step response. The variance in this computed value for a given trial compared to the previous n trials can be used. Alternative methods of determining a threshold for success for step response to a given perturbation are readily defined, such as the number of trials in a row for achieving the target step response.

After a individual successfully passes the stable gait response test for a given velocity change perturbation, that velocity change is increased until individual is able to successfully complete a prescribed velocity change at 108. The height of the obstacle is progressively incrementally increased up to a prescribed height at 106. The initial distance of the second obstacle from the individual is progressively incrementally increased at 102 up to a prescribed distance. Intrinsic individual parameters, such as height, body center of mass, age, and flexibility, are used to determine, for that individual, the maximum velocity change, the maximum obstacle height and the maximum initial obstacle distance for that individual. Once the individual has exceeded the predetermined maximum velocity change with stable gait step response at 108 and acceptably low variability between sessions, the disturbance events are stopped at 110 and they are moved to Stage 6 in the protocol at 112 of the method of the present invention. It should also be noted that in the case where the disturbance event is large and is intended to be a slip incident, Stage 5 may be omitted.

Stage 6—Stable Gait After Initial Steady State Locomotion and Large Disturbance

Figure 13:
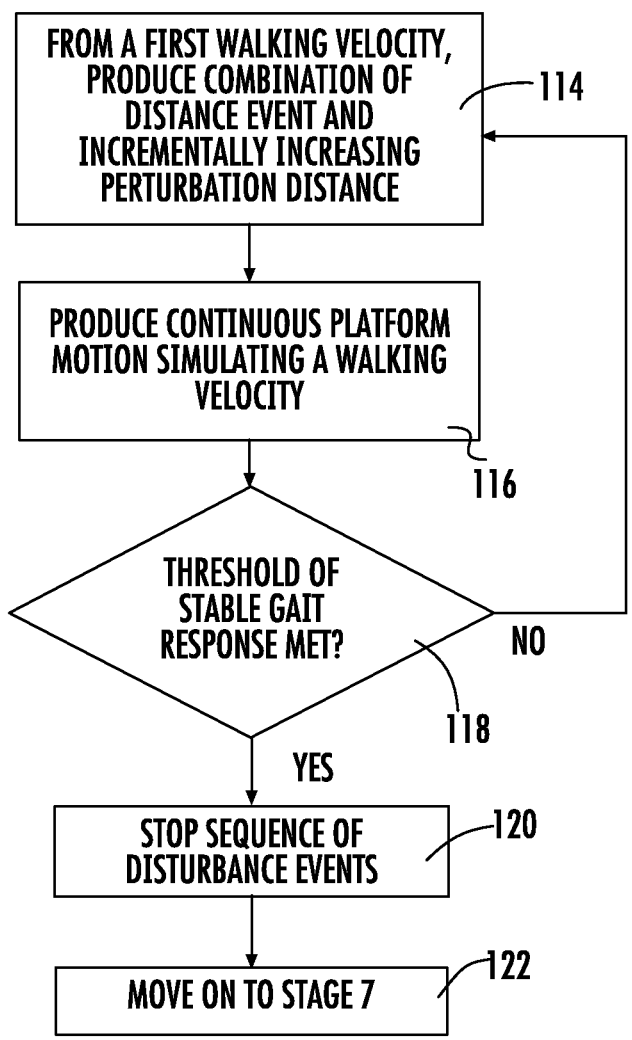
FIG. 13 is a flow chart illustrating the execution of Stage 6 of the method of the present invention.

In FIG. 13, the individual starts at an initial steady state locomotion velocity (velocity 1). A large disturbance is introduced at a random time. The disturbance causes the platform to accelerate to a prescribed disturbance velocity (velocity 2) before returning to a second steady state locomotion velocity (velocity 3). The maximum time for this change in the platform velocity (the time between when the change from velocity 1 is initiated and velocity 3 is achieved) is less than about 500 ms, and is more typically in the range of about 100 to about 200 ms. Velocity 3 may or may not be different from velocity 1. The three velocities and their timing are called the velocity profile.

A stable gait response is sought from the individual. If they are able to achieve a stable gait within a predetermined number of steps, the trial is considered successful. If the individual requires more than the predetermined number steps to achieve stable gait or if the individual falls, the velocity profile is repeated.

Trials are be repeated within a session or across sessions until the variability in step response following a given perturbation displacement and profile are below a target value or threshold. For example, a minimization function relating step length and step width may be employed to calculate a residual value for step response. This value is be called a target step response. The variance in this computed value for a given trial compared to the previous n trials can be used. Alternative methods of determining a threshold for success for step response to a given perturbation are readily defined, such as the number of trials in a row for achieving the target step response.

After a individual successfully passes the stable gait response test for a given velocity profile perturbation, parameters in that velocity profile are incrementally increased until individual is able to successfully complete a prescribed velocity profile. For example, the magnitude of the disturbance (defined as the difference between velocity 1 and velocity 2) is progressively and incrementally increased up at 114 to a prescribed disturbance magnitude, velocity 1 is progressively and incrementally increased up to a prescribed velocity and velocity 3 is incrementally increased up to a prescribed velocity to achieve motion to simulate walking at 116.

Intrinsic individual parameters, such as height, body center of mass, age, and flexibility, are used to determine the final velocity profile for that individual. Once the individual has exceeded the predetermined final velocity profile with stable gait step response at 118, the disturbance events are stopped at 120 and they are moved to Stage 7 in the protocol of the method of the present invention.

Figure 14:
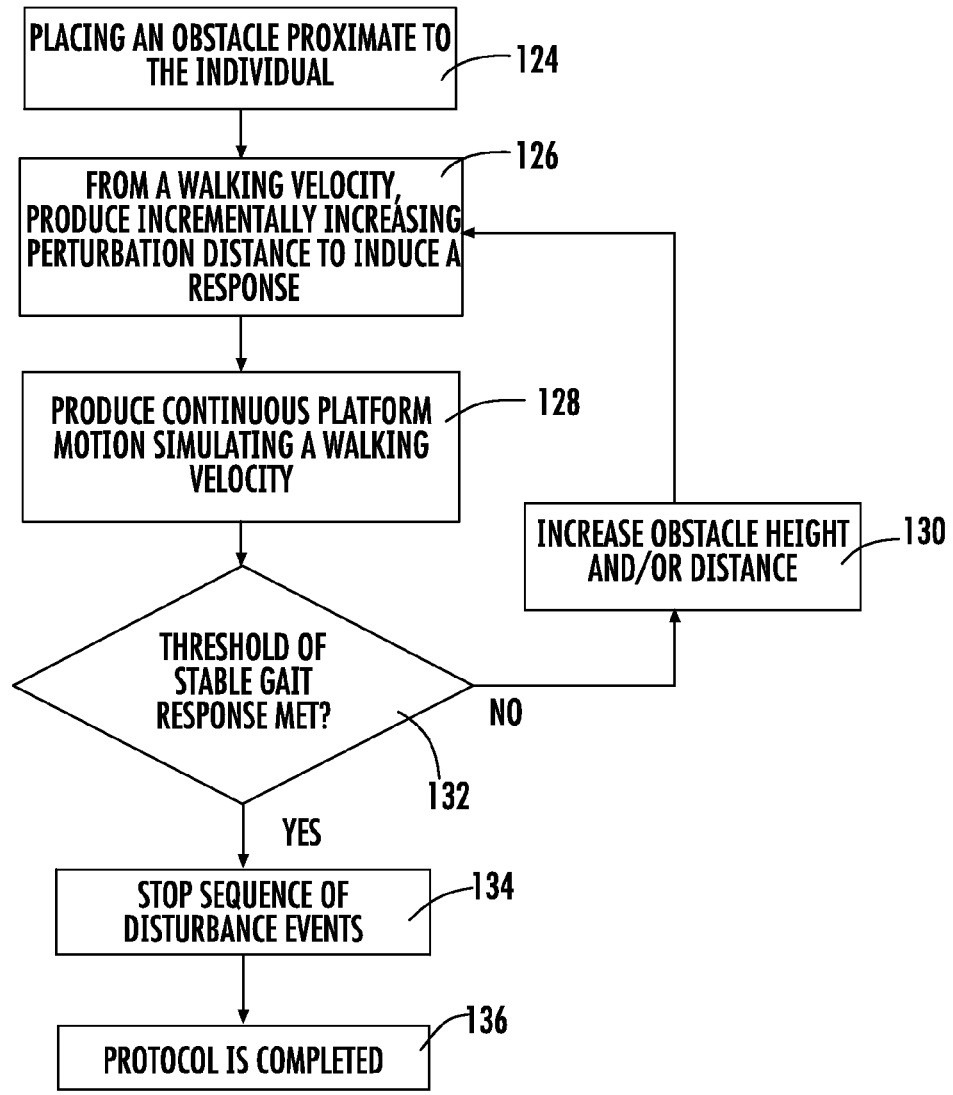
FIG. 14 is a flow chart illustrating the execution of Stage 7 of the method of the present invention.

Stage 7—Stable Gait After Initial Steady State Locomotion and Large Disturbance With Third Obstacle In FIG. 14, the individual 14 starts at an initial steady state locomotion velocity (velocity 1). A large disturbance is introduced at a random time. In concert with the large disturbance, a third obstacle is placed proximate to the individual at 124, such as ahead of the individual, in the direction so that the perturbation forces them to make a step response. The third obstacle may be the same as the first obstacle and/or the second obstacle. Alternatively, all three obstacles may be different than one another. The disturbance causes the platform to accelerate to a prescribed disturbance velocity (velocity 2) before returning to a second steady state locomotion velocity (velocity 3). The maximum time for this change in the platform velocity (the time between when the change from velocity 1 is initiated and velocity 3 is achieved) is less than about 500 ms, and is more typically in the range of about 100 to about 200 ms. Velocity 3 may or may not be different from velocity 1. The three velocities and their timing are called the velocity profile.

The distance that the third obstacle is initially placed from the individual can vary between zero (i.e. touching the individual) and a prescribed maximum obstacle distance from individual. Intrinsic individual parameters, such as height, body center of mass, age, and flexibility are used to determine a maximum obstacle distance from the individual for that individual. Similar to the first obstacle and the second obstacle, the third obstacle can either be real or virtual. In the preferred embodiment of the present invention, the third obstacle is about 5 cm high but it can be in the range of about 1 mm up to about one half of the body height of the individual.

A stable gait response is sought from the individual. If the individual is able to achieve a stable gait within a predetermined number of steps, the trial is considered successful. If the individual requires more than the predetermined number of steps to achieve stable gait or if the individual falls, the velocity profile is repeated.

Trials are be repeated within a session or across sessions until the variability in step response following a given perturbation displacement and profile are below a target value. For example, a minimization function relating step length and step width may be employed to calculate a residual value for step response. This value is called a target step response. The variance in this computed value for a given trial compared to the previous n trials can be used. Alternative methods of determining a threshold for success for step response to a given perturbation are readily defined, such as the number of trials in a row for achieving the target step response.

After a individual successfully passes the stable gait response test for a given velocity profile perturbation, parameters in that velocity profile are incrementally increased until the individual is able to successfully complete a prescribed velocity profile. For example, the magnitude of the disturbance (defined as the difference between velocity 1 and velocity 2) is incrementally increased at 126 up to a prescribed disturbance magnitude to produce a motion simulating a walking velocity at 128. Velocity 1 is incrementally increased up to a prescribed velocity and velocity 3 is incrementally increased up to a prescribed velocity. The height of the third obstacle is progressively increased up to a prescribed height at 130 and the initial distance of the third obstacle from the individual is progressively increased up to a prescribed distance.

Intrinsic individual parameters, such as height, body center of mass, age, and flexibility, are used to determine the final velocity profile (including maximum velocity 1, maximum velocity 2, and maximum magnitude of disturbance), maximum obstacle height, maximum initial obstacle distance for that individual. Once the individual has exceeded the predetermined final velocity profile with stable gait step response at 132 and acceptably low variability between sessions, the disturbance events are stopped at 134 and protocol of the method of the present invention is completed at 136. It should also be noted that in the case where the disturbance event is large and is intended to be a slip incident, Stage 7 may be omitted.

Figure 15C:
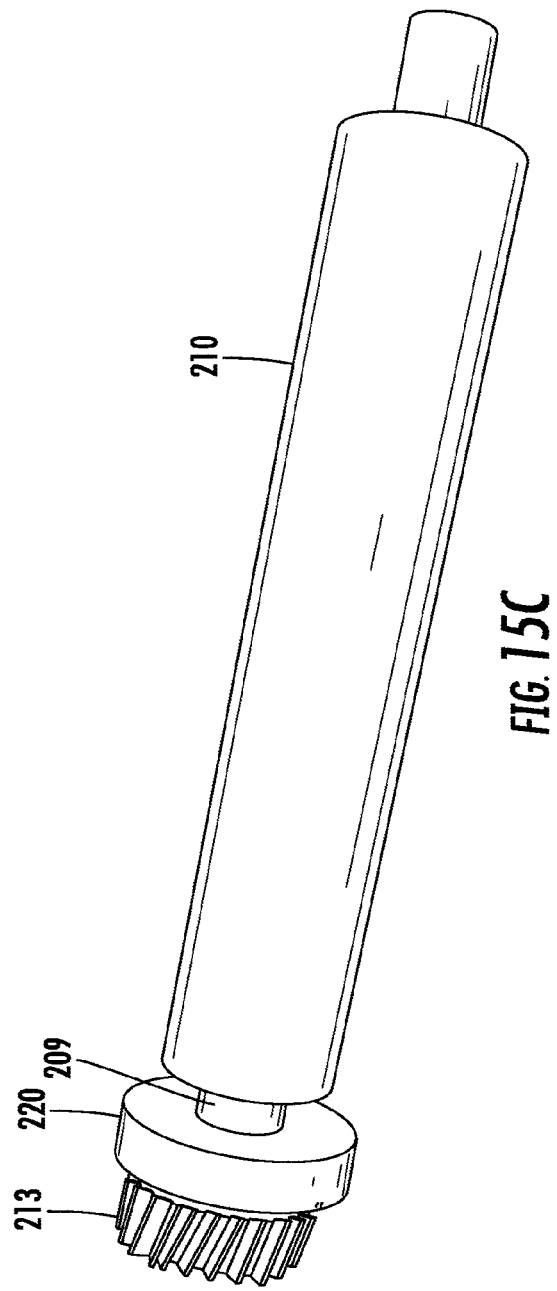
FIG. 15C is a perspective view of a motor transmission that is inline with the MR clutch and drive roller.

Referring now to FIGS. 15A, 15B, 15C and 20, a lateral deck 200 of the present invention is controlled by a DC rack-and-pinion drive 202, with center under deck, that slides on a low friction polymer surface 204 that is fixed to an aluminum sub-frame 206. The drive motor 208 and rollers 210 are all mounted on the deck 200 to maintain alignment of the walkway belt via drive pulleys 211. A locking mechanism prevents lateral motion when desired. At a specific phase of the gait cycle, the lateral mechanism moves the entire deck assembly 200 relative to the sub-frame 206 using the DC rack-and-pinion drive at a specified velocity and distance delivering a lateral perturbation to the user. The lateral deck 200 of FIGS. 15A, 15B and 15C is a further embodiment of the present invention compared to the deck shown in FIG. 1.

To the end user, the system resembles a treadmill and has similar functionality as a traditional treadmill, but with the added highly controlled perturbations that are superimposed with treadmill velocity at, for example, specific phases in the gait cycle or from external triggers, to elicit a targeted user response. Perturbations are high acceleration changes in gait velocity that last less than 500 msec and preferably less than 150 ms.

Figure 20:
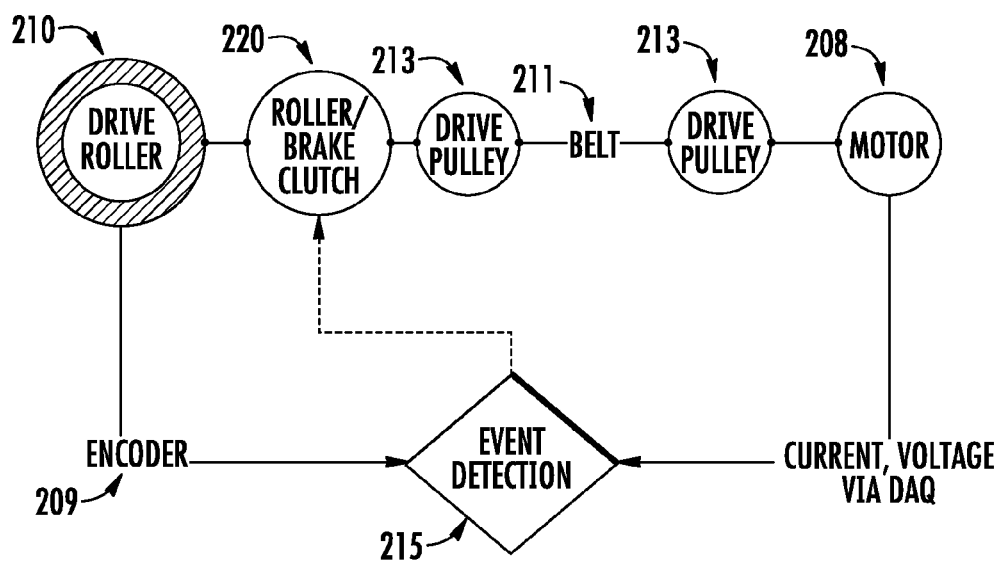
FIG. 20 is a flowchart illustrating the interrelation of the components used for delivering and controlling perturbations in accordance with the present invention.

In one embodiment of the present invention, referring to FIGS. 15A, 15B and 15C and representationally shown in FIG. 20, a novel roller/brake clutch system 220, alternatively referred to as a slip clutch system, such as a electromagnetic (EM) or magnetorheological (MR) roller/brake clutch, connected between drive pulley 213 and drive roller 210 is adapted to existing AC motors currently used in commercial treadmills to provide a microprocessor controlled mechanism for precise control of perturbation displacement, velocity, and acceleration. For example, a roller/break clutch 220 controls the slip characteristics at the desired timing for the perturbation. In this embodiment, the perturbations are achieved by utilizing the horizontal reaction force generated during stance to overpower the low-inertia rollers 210 and coupled slip clutch system 220 in FIG. 15C.

It should be understood that alternate embodiments for creating the desired perturbation kinematics exist. The equipment shown and discussed herein are examples of how the method of the present invention can be carried out.

In a preferred embodiment of the present invention, motion of the treadmill platform 204 has dimensions 5.08 cm in 0.5 secs minimum in all directions. The maximum response time from trigger to release roller 210 to cause a dynamic perturbation is preferably 100 msec, and the maximum response time to re-engage roller 210 to achieve total desired perturbation motion is preferably 100 msec.

In one embodiment, a servo-driven rack-and-pinion drive 202 is provided for lateral translation of the support surface. When coupled with the roller-clutch system 220 and the treadmill with lateral deck 200 itself, multi-axis perturbation is readily achieved and controlled. The treadmill with lateral deck 200 and motor drive 208 can attach to the rack-and-pinion system 202 and rest on ultra-low friction plates 204 for unrestricted motion.

The present invention includes a novel system and method for delivering the controlled perturbations of the apparatus in FIGS. 1 and 15 at specific timing based on event detection algorithms that provide information related to the kinematics of the user. The present invention also includes a novel apparatus and method for delivering the controlled perturbations of the apparatus at specific timing based event detection of external triggers, such as a manual switch, audio cues, visual cues, or tactile cues. The perturbation system can be programmed to allow constant or changing amplitude and constant or changing frequency of perturbations that change from step to step or over a period of time. In accordance with the present invention, perturbations that require a response, such as a step, by the user but which do not necessarily induce a fall. These are imbalances for which the body must and does respond to, whatever their direction. In the preferred embodiment using a motor drive 208, the magnitude and timing of the perturbations delivered by the roller/brake clutch mechanism 220 are pre-programmed for the perturbation profiles desired.

Event detection algorithms 258 provide a trigger output that initiates a perturbation profile. FIG. 20 represents one embodiment of this novel system and method of detecting events and delivering controlled perturbations, whereby the roller/brake clutch system 220 in FIG. 15C is integrated with a motor drive 208 and roller encoder 209 to provide the controlled perturbation together with event detection based on real-time feedback from the components, external cues and specific timing relating to various phases of the gait cycle, such as but not limited to heel strike or toe off. When the event detection algorithm 215 detects a trigger, the prescribed perturbation is executed by the perturbation apparatus, for example, the motor drive 208 and the roller-clutch/brake mechanism 220 via the drive pulleys 213 and belt 211.

Detection of heel strike during walking can be used as an example to demonstrate the steps in the novel system and method for delivering the controlled perturbations included in an event detection algorithm. The event detection algorithm is programmed to issues trigger signal or signals to deliver the prescribed perturbation at the $1^{st}$, $2^{nd}$, nth detected event, such as heel strike, or randomly selected based on a normal or other statistical distribution of detected events. Alternatively and additionally, the trigger can occur due to an external input such as from a switch. The process for determining when a perturbation should be delivered is shown in the flow chart of FIG. 17 and is explained herein.

Figure 16:
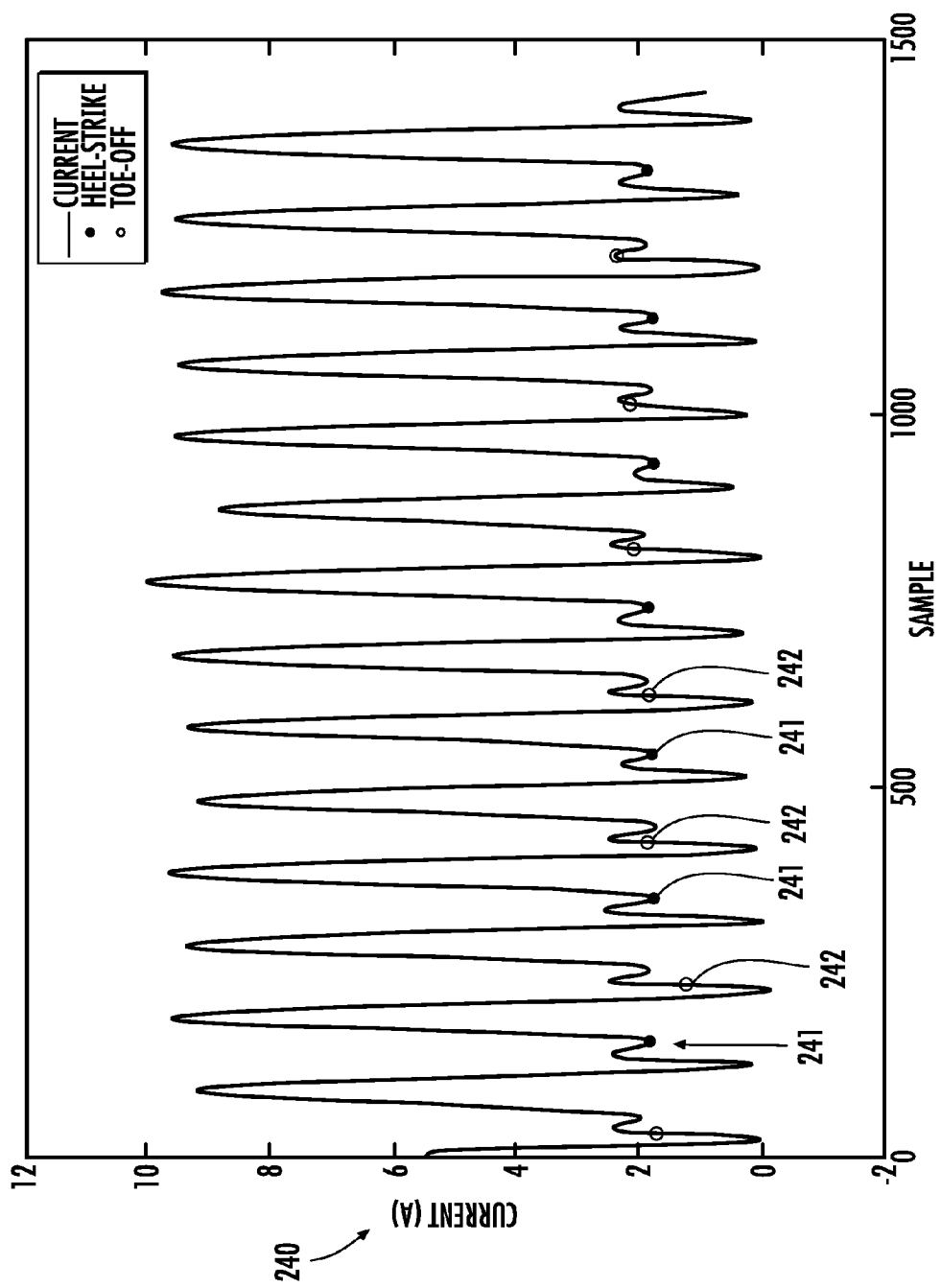
FIG. 16 is a graphical representation of an algorithm according to the present invention that performs real-time event (e.g. heelstrike or toe-off) detection based on motor current.

In one embodiment, heel strikes can be detected by monitoring motor current. A graph of motor current 240 versus time can be seen in FIG. 16. At the moment of heel strike 241, as in FIG. 16, there is a horizontal resultant force that opposes the treadmill belt normal movement resulting in a decrease in belt velocity. Toe-off 242 is also shown on graph 240. To maintain the belt at a constant velocity, the motor drive 208 increases the motor current to maintain the constant velocity in the presence of the increased drag. This represents a significant increase in motor current (I) with respect to time (dI/dt), which can be detected so that, for example, the positive peak in motor current derivative (dI/dt) defines when the heel strike occurs.

FIGS. 18A-18F show various data derived from motor current motor position which can be used to identify when a heel strike 241 or toe-off 242 event has occurred thereby warranting delivery of a perturbation. FIGS. 19A-19B illustrate such identification of an event using motor current only when heel strike 241 and toe-off 242 events occur resulting from the monitoring the motor current independently alone or together with other variables such as the time rate of change of motor current. In this case, the moment of heel strike 241 and toe-off 242 can be ascertained from monitoring the motor current parameter to identify the detection event and cause a perturbation trigger.

Figure 17:
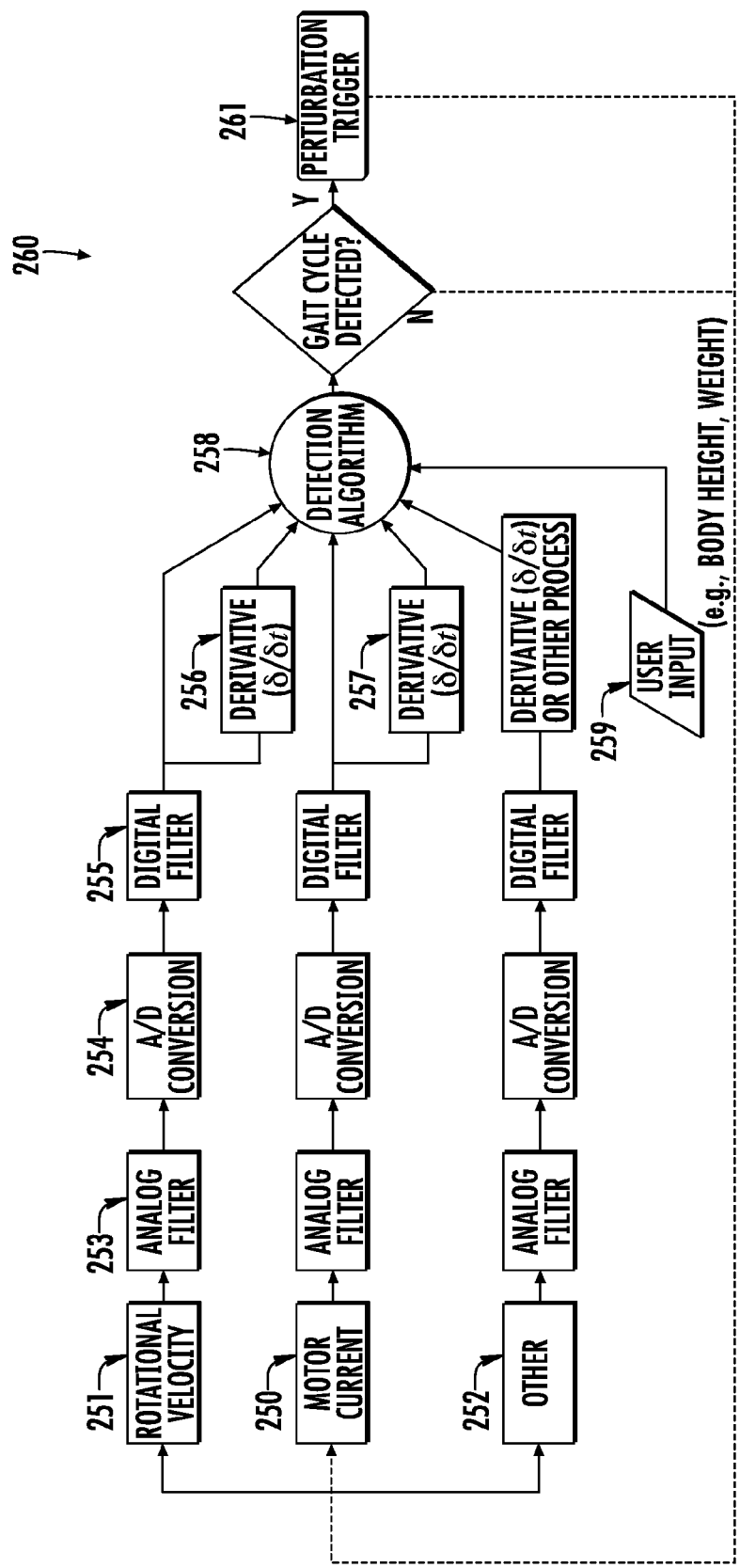
FIG. 17 is a flowchart illustrating a process for detecting gait phase, such as heel strike and toe off, in accordance with the present invention.
Figure 18A:
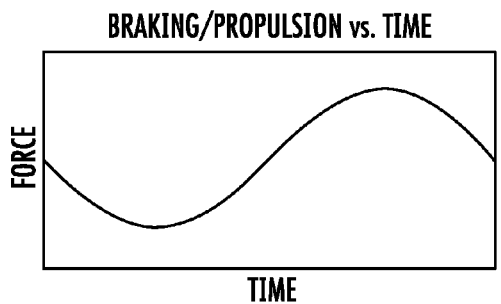
FIGS. 18A-F illustrate various graphs of data collected for a one step cycle in accordance with the gait phase detection process in accordance with the present invention.
Figure 18B:
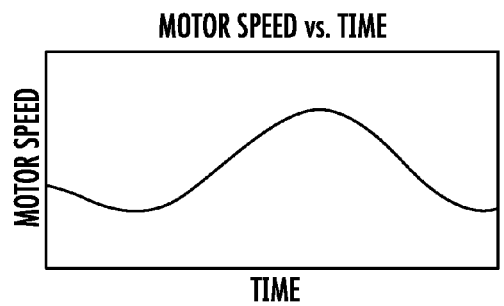
Figure 18C:
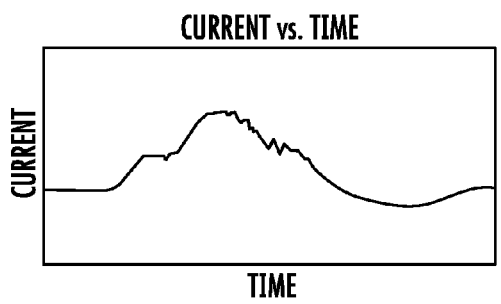
Figure 18D:
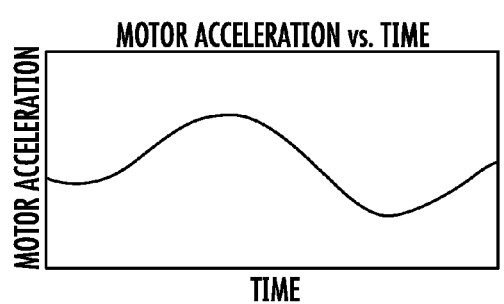
Figure 18E:
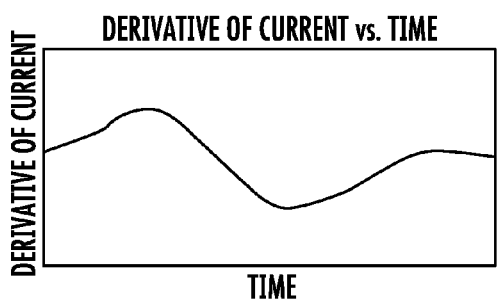
Figure 18F:
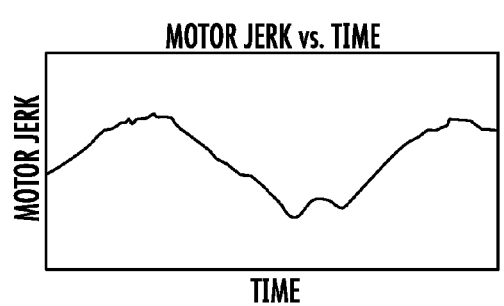

In this embodiment, representationally shown in FIG. 17, the motor current 250 is detected by a sensor 205 in FIG. 15B. This sensor 205 can be any current monitoring sensor such a hall effect sensor. In one embodiment, the output of sensor 205 is passed through an analog filter 253, such as a single pole RC low pass filter with a −3 db point around 10 Hz. The motor current signal 250 is preferably amplified by a gain, and offset relative the zero current output level of the sensor 205 and, in this embodiment, converted through analog to digital conversion 254 to a digital signal for processing. This digital value is processed through a digital filter 255, such as a kernel smoothing algorithm which applies half sine coefficients over a variable width range of samples. The heel strike feature is detected from this smoothed output in the event detection algorithm 258. In this case, heel strike is detected by finding the positive peak of the current signal derivative 257.

Alternate variables that can be used independently or together with the motor current include motor voltage, and motor power. Each of these measured or computed variables provides a time history that provides unique information about the loads and timing of loads applied to the motor 208, which in turn are representative of different phases of the gait cycle or other information relating to the gait cycle. Similar measurements and computational analysis for detecting kinematic events can be performed for loads placed on motors during motion of other body joints other than lower extremity joints associated with gait. For example, motion of the trunk or upper extremity and phases of the such motion, such as shoulder kinematics or spinal kinematics, can be detected by the algorithm of the present invention.

Additional embodiments for detection of kinematic events of the treadmill apparatus incorporate data from other sensors 207 such as linear or rotational encoders which provide data including but not limited to velocity, acceleration, and jerk of the moving elements of the apparatus. These sensors 207 may be, for example, located on the rollers 210 of the treadmill 200 or on other exercise equipment where kinematic motion is measurable. For example, a rotational encoder 209 may be attached to the roller drive 210 to record roller 210 and motor 208 rotational displacement. The time rate of change of the roller drive 210 and motor 208 rotational displacement is the rotational velocity 251 in FIG. 17 and the time rate of change of velocity 251 is the rotational acceleration 256. These data are used alone, or, as desired, fused with data such as motor current 250 and time rate of change of motor current 257 and other sensor 207 data output 252 and time rate of change of this data output 252 to provide more robust detection algorithms 258. These algorithms may optionally use digital filtering 255, such as Kalman or complementary filters.

The detection algorithm 258 may use one or more of these variables. For example, linear and rotational encoder data from a motor combined with current and derivatives of these data can be combined to create latent variables, using Independent Component Analysis, Principal Component Analysis or other data reduction techniques, on which feature extraction and feature detection can be performed to simplify data processing for the detection algorithm. Other embodiments of the data algorithm 258 for detecting gait phase events or events related to motion of a body joint incorporate Markov chains, Bayesian statistics, neural networks, or similar approaches that provide sensor fusion and real-time feature extraction.

Additionally, user input data 259, such as user body height, and weight, and/or an external switch, can be input as part of the event detection algorithm 258. When the event detection algorithm 258 detects an event 260, a perturbation trigger 261 is initiated. In a preferred embodiment, the detection algorithm 258 detects and triggers a perturbation within 40 ms of the detected event.

The event detection algorithm 258 also identifies events that can occur as a percentage of step time (e.g. mid-stance). In one embodiment, this algorithm is, based on average step time based on subject and walking speed during a warm-up phase. During this phase, each step is used (n>30) to determine an average step time. In one use method, the user can select a percent of stance phase, or percent of average step time, at which to issue a trigger (eg. 0-100% from heelstrike to toeoff). Alternatively, such a trigger time can be selected randomly from between 0-100% of the gait cycle from heel strike to toe off, including but not limited to the braking phase and the propulsion phase of stance. Additionally, this gait phase detection system 200 can be used to control and to change the treadmill speed based on braking phase (time and force as measured by motor current and propulsion phase. If the braking phase impulse is greater than propulsion phase impulse (adjusted for treadmill running), then the treadmill belt (not shown) slows down. If the braking phase impulse is less than the propulsion phase impulse (adjusted for treadmill running), then the treadmill belt speeds up. The application of perturbations at various phases of the gait cycle allows for training to modulate the stretch reflex/arc of the muscles crossing a body joint in the lower extremity. The same approach exists for training at different ranges of motion for a body joint in the upper extremity.

It should be understood that the algorithms of the present invention are executed by software that is located and stored on a storage device in computer hardware. The computer hardware preferably includes the typical storage, such as hard drive, with operating system thereon, with memory and input and output capability so computer data may be transferred between the computer running the algorithm and another electronic device. The sensors and other equipment electrically and physically interface with the computer hardware. Any type of operating system and computer language may be employed.

Figure 21:
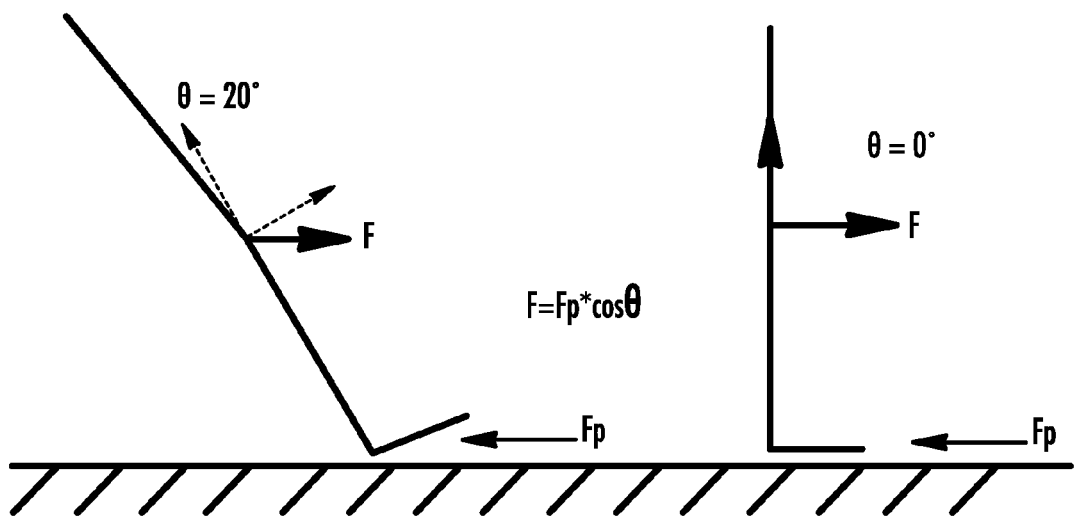
FIG. 21 illustrates the effects of delivering perturbations forces at different phases of the gait cycle such as heelstrike and midstance, resulting in different kinetic and kinematic responses.

The perturbations enable individuals to rapidly learn how to modify motor performance Referring now to FIG. 21, the same perturbation force Fp applied at different phases of the gait cycle, represented here as knee angle theta, results in different forces F applied at the knee, which in turn causes different kinematic response of the knee and other joints. The anterior force F at the knee is dependent on the knee angle theta and the applied perturbation force Fp. For human locomotion, knee angle during walking/running follows a very predictable pattern. Likewise, the perturbations can be applied to any joint based on the current position, velocity, or acceleration of the joint, independent of gait. This is particularly relevant for upper body neuromuscular training paradigms.

The invention provides a method of providing a timed perturbation to the apparatus 10 or 200 based on external cues from a musical source or other external source (not shown). Music drives exercise profiles (speed, elevation, perturbation frequency/magnitudes, intensity, and the like)—real-time modification of playlist based on what is being done. Music feedback can be used by the present invention as a behavioral modifier.

In view of the foregoing, a new and novel system and apparatus is provided that captures biomechanical data of body movement during a disturbance event, such as a slip or trip incident or other event experience by a part of the body. A disturbance event is simulated by a treadmill-based apparatus or other device. Data collected is used to compute a wide array of parameters associated with body movement to better and more fully understand body movement during a disturbance event. Such parameters are to be studied to determine and evaluate step responses to a disturbance event. As a result, a new and novel method of fall prevention training can be provided to the person to reduce the likelihood of falling following a disturbance event. As a result, a new and novel neuromuscular training system for body joints can be provide to increase dynamic stiffness of the joint, and to reduce the likelihood of injury to the joint caused by excessive motion.

It would be appreciated by those skilled in the art that various changes and modifications can be made to the illustrated embodiments without departing from the spirit of the present invention. All such modifications and changes are intended to be covered by the appended claims.

What is claimed is:

1. A method of training, comprising the steps of:
   providing a platform configured to support an individual standing thereon;
   moving the platform, with the individual thereon, to cause the individual to achieve a continuous walking gait;
   moving the platform to create a disturbance event having a duration of less than 500 ms that induces instability in a joint of the individual as part of a continuous walking gait.

2. The method of claim 1, further comprising the steps of:
   recording the response of the individual;
   locating a plurality of sensors proximate to the individual and the platform; outputting data from the plurality of sensors;
   collecting and storing the data during a disturbance event; and
   outputting the data.

3. The method of claim 1, wherein the platform is moved to create a disturbance event manually.

4. The method of claim 1, wherein the platform is moved to create a disturbance event at predetermined intervals.

5. The method of claim 1, wherein the platform is moved to create a disturbance event according to a preset script.

6. A training apparatus, comprising:
a platform configured to support an individual standing thereon;
the platform, with an individual thereon, configured to cause the individual to achieve a continuous walking gait;
the platform being capable of moving to create a disturbance event having a duration of less than 500 ms that induces instability in a joint of the individual as part of a continuous walking gait.

7. The training apparatus of claim 6, further comprising:
means for recording a response of the individual;
a plurality of sensors proximate to the individual and the platform;
means for outputting data from the plurality of sensors;
means for collecting and storing the data during the disturbance event; and
means for outputting the data.

8. The training apparatus of claim 6, wherein the platform is configured to move to create a disturbance event manually.

9. The training apparatus of claim 6, wherein the platform is configured to move to create a disturbance event at predetermined intervals.

10. The training apparatus of claim 6, wherein the platform is configured to move to create a disturbance event according to a preset script.

* * * * *